(12) United States Patent
Peterson et al.

(10) Patent No.: US 9,724,512 B2
(45) Date of Patent: Aug. 8, 2017

(54) IMPLANTABLE ELECTROACUPUNCTURE SYSTEM AND METHOD FOR TREATING PARKINSON'S DISEASE AND ESSENTIAL TREMOR THROUGH APPLICATION OF STIMULUI AT OR NEAR AN ACUPOINT ON THE CHOREA LINE

(71) Applicant: Valencia Technologies Corporation, Valencia, CA (US)

(72) Inventors: David K. L. Peterson, Valencia, CA (US); Stacy Greiner Chambliss, Los Angeles, CA (US)

(73) Assignee: Valencia Technologies Corporation, Valencia, CA (US)

( * ) Notice: Subject to any disclaimer, the term of this patent is extended or adjusted under 35 U.S.C. 154(b) by 16 days.

(21) Appl. No.: 14/609,108

(22) Filed: Jan. 29, 2015

(65) Prior Publication Data

US 2015/0148864 A1 May 28, 2015

Related U.S. Application Data

(63) Continuation-in-part of application No. 13/765,572, filed on Feb. 12, 2013, now Pat. No. 9,433,786, which
(Continued)

(51) Int. Cl.
*A61N 1/00* (2006.01)
*A61N 1/36* (2006.01)
(Continued)

(52) U.S. Cl.
CPC ....... *A61N 1/36067* (2013.01); *A61N 1/0504* (2013.01); *A61N 1/0529* (2013.01);
(Continued)

(58) Field of Classification Search
CPC .............. A61N 1/0534; A61N 1/36067; A61N 1/0504; A61N 1/0529; A61N 1/37205;
(Continued)

(56) References Cited

U.S. PATENT DOCUMENTS 4,031,899 A 6/1977 Renirie
4,157,720 A 6/1979 Greatbatch
(Continued)

FOREIGN PATENT DOCUMENTS

EP 1145736 A2 10/2001
WO WO 01/41869 A1 6/2001
WO WO 02/00294 A1 1/2002

OTHER PUBLICATIONS

Shulman, Lisa M., et al. "Acupuncture therapy for the symptoms of Parkinson's disease." Movement disorders 17.4 (2002): 799-802.*
(Continued)

*Primary Examiner* — Lindsey G Wehrheim
(74) *Attorney, Agent, or Firm* — ALG Intellectual Property, LLC

(57) ABSTRACT

An implantable electroacupuncture device (IEAD) treats Parkinson's disease or Essential Tremor through application of stimulation pulses applied to at least one of the acupoints on the chorea line. The IEAD includes an hermetically-sealed implantable electroacupuncture (EA) device and a conduit extending therefrom. At least one electrode is located on the outside of the housing. At least one electrode is located at an opening formed through the conduit. The housing contains a primary power source and pulse generation circuitry. A sensor wirelessly senses externally-generated operating commands, such as ON, OFF and AMPLITUDE. The pulse generation circuitry generates stimulation pulses. The stimulation pulses are applied to the specified
(Continued)

acupoint or nerve through the electrodes in accordance with a specified stimulation regimen.

17 Claims, 24 Drawing Sheets

Related U.S. Application Data is a continuation-in-part of application No. 13/630,522, filed on Sep. 28, 2012, now Pat. No. 9,173,811.

(51) Int. Cl.
    *A61N 1/05*     (2006.01)
    *A61N 1/372*     (2006.01)
    *A61N 1/375*     (2006.01)
    *A61N 1/378*     (2006.01)

(52) U.S. Cl.
    CPC ...... *A61N 1/37205* (2013.01); *A61N 1/36125* (2013.01); *A61N 1/36153* (2013.01); *A61N 1/36157* (2013.01); *A61N 1/36175* (2013.01); *A61N 1/3756* (2013.01); *A61N 1/3758* (2013.01); *A61N 1/3782* (2013.01)

(58) Field of Classification Search
    CPC ............ A61N 1/36125; A61N 1/36153; A61N 1/36157; A61N 1/36175; A61N 1/3756; A61N 1/3758; A61N 1/3782
    See application file for complete search history.

(56) References Cited

U.S. PATENT DOCUMENTS

| | | | |
|---|---|---|---|
| 4,345,604 A | 8/1982 | Renirie |
| 4,528,072 A | 7/1985 | Kurosawa |
| 4,535,784 A | 8/1985 | Rohlicek |
| 4,566,064 A | 1/1986 | Whitaker |
| 5,195,517 A | 3/1993 | Chen |
| 5,199,428 A | 4/1993 | Obel |
| 5,211,175 A | 5/1993 | Gleason |
| 5,250,068 A | 10/1993 | Ideguchi |
| 5,251,637 A | 10/1993 | Shalvi |
| 5,372,605 A | 12/1994 | Adams |
| 5,544,656 A | 8/1996 | Pitsillides |
| 5,609,617 A | 3/1997 | Shealy |
| 5,707,400 A | 1/1998 | Terry |
| 5,891,181 A | 4/1999 | Zhu |
| 6,006,134 A | 12/1999 | Hill |
| 6,178,352 B1 | 1/2001 | Gruzdowich |
| 6,393,324 B2 | 5/2002 | Gruzdowich |
| 6,522,926 B1 | 2/2003 | Kieval |
| 6,658,298 B2 | 12/2003 | Gruzdowich |
| 6,735,475 B1 | 5/2004 | Whitehurst |
| 6,839,596 B2 | 1/2005 | Nelson |
| 6,950,707 B2 | 9/2005 | Whitehurst |
| 6,978,174 B2 | 12/2005 | Gelfand |
| 7,003,352 B1 | 2/2006 | Whitehurst |
| 7,013,177 B1 | 3/2006 | Whitehurst |
| 7,046,499 B1 | 5/2006 | Imani |
| 7,136,701 B2 | 11/2006 | Greatbatch |
| 7,155,279 B2 | 12/2006 | Whitehurst |
| 7,162,303 B2 | 1/2007 | Levin |
| 7,171,266 B2 | 1/2007 | Gruzdowich |
| 7,203,548 B2 | 4/2007 | Whitehurst |
| 7,292,890 B2 | 11/2007 | Whitehurst |
| 7,321,792 B1 | 1/2008 | Min |
| 7,373,204 B2 | 5/2008 | Gelfand |
| 7,440,806 B1 | 10/2008 | Whitehurst |
| 7,444,180 B2 | 10/2008 | Kuzma |
| 7,610,100 B2 | 10/2009 | Jaax |
| 7,620,451 B2 | 11/2009 | Demarais |
| 7,657,316 B2 | 2/2010 | Jaax |
| 7,962,219 B2 | 6/2011 | Jaax |
| 2002/0016568 A1 | 2/2002 | Lebel |
| 2003/0078642 A1* | 4/2003 | Malaney ............... A61H 39/002 607/115 |
| 2003/0158588 A1 | 8/2003 | Rizzo |
| 2003/0171790 A1 | 9/2003 | Nelson |
| 2003/0187485 A1 | 10/2003 | Sturman |
| 2003/0195583 A1 | 10/2003 | Gruzdowich |
| 2003/0195585 A1 | 10/2003 | Gruzdowich |
| 2003/0220668 A1 | 11/2003 | Shealy |
| 2003/0236558 A1 | 12/2003 | Whitehurst |
| 2005/0107832 A1 | 5/2005 | Bernabei |
| 2005/0228460 A1 | 10/2005 | Levin |
| 2005/0234533 A1 | 10/2005 | Schulman |
| 2006/0041283 A1 | 2/2006 | Gelfand |
| 2006/0184209 A1 | 8/2006 | John |
| 2007/0005119 A1 | 1/2007 | Crohn |
| 2007/0219595 A1 | 9/2007 | He |
| 2007/0255319 A1 | 11/2007 | Greenberg |
| 2007/0265680 A1 | 11/2007 | Liu |
| 2008/0015572 A1 | 1/2008 | Johnson |
| 2008/0091255 A1 | 4/2008 | Caparso |
| 2008/0097529 A1 | 4/2008 | Parramon |
| 2009/0192555 A1 | 7/2009 | Schleicher |
| 2009/0210026 A1 | 8/2009 | Solberg |
| 2009/0292341 A1 | 11/2009 | Parramon |
| 2010/0042137 A1 | 2/2010 | Oronsky |
| 2010/0069992 A1 | 3/2010 | Aghassian |
| 2010/0211132 A1 | 8/2010 | Nimmagadda |
| 2010/0324624 A1 | 12/2010 | Chang |
| 2010/0327887 A1 | 12/2010 | Denison |
| 2011/0106219 A1 | 5/2011 | Cauller |
| 2011/0106220 A1 | 5/2011 | DeGiorgio |
| 2011/0112603 A1 | 5/2011 | DeGiorgio |
| 2011/0172739 A1 | 7/2011 | Mann |
| 2011/0218589 A1 | 9/2011 | DeGiorgio |
| 2011/0218590 A1 | 9/2011 | DeGiorgio |
| 2012/0022612 A1 | 1/2012 | Littlewood |
| 2012/0259390 A1 | 10/2012 | Canion |
| 2013/0041396 A1 | 2/2013 | Ryotokuji |

OTHER PUBLICATIONS

Song, Kiseok, "The Compact Electro-Acupuncture System for Multi-Modal Feedback Electro-Acupuncture Treatment," 34th Annual International Conference of the IEEE EMBS, San Diego, CA, USA, Aug. 28-Sep. 1, 2012.

\* cited by examiner

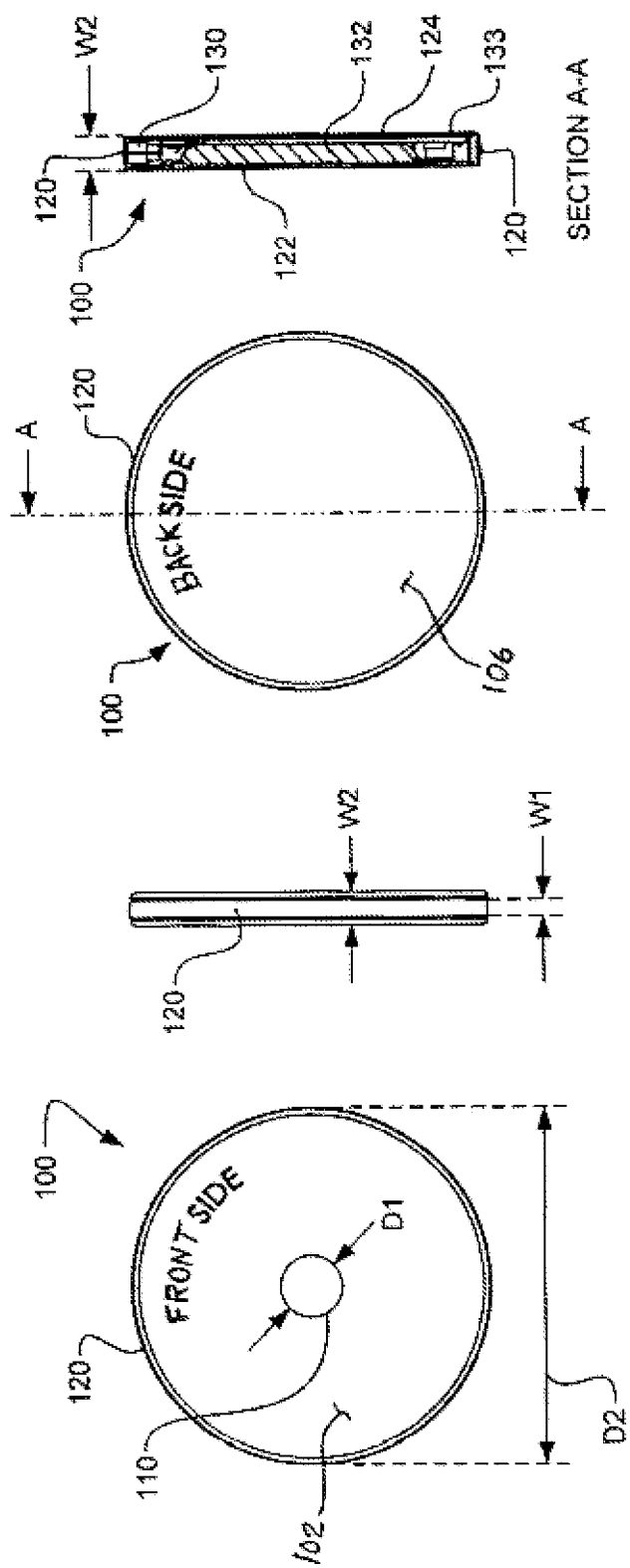

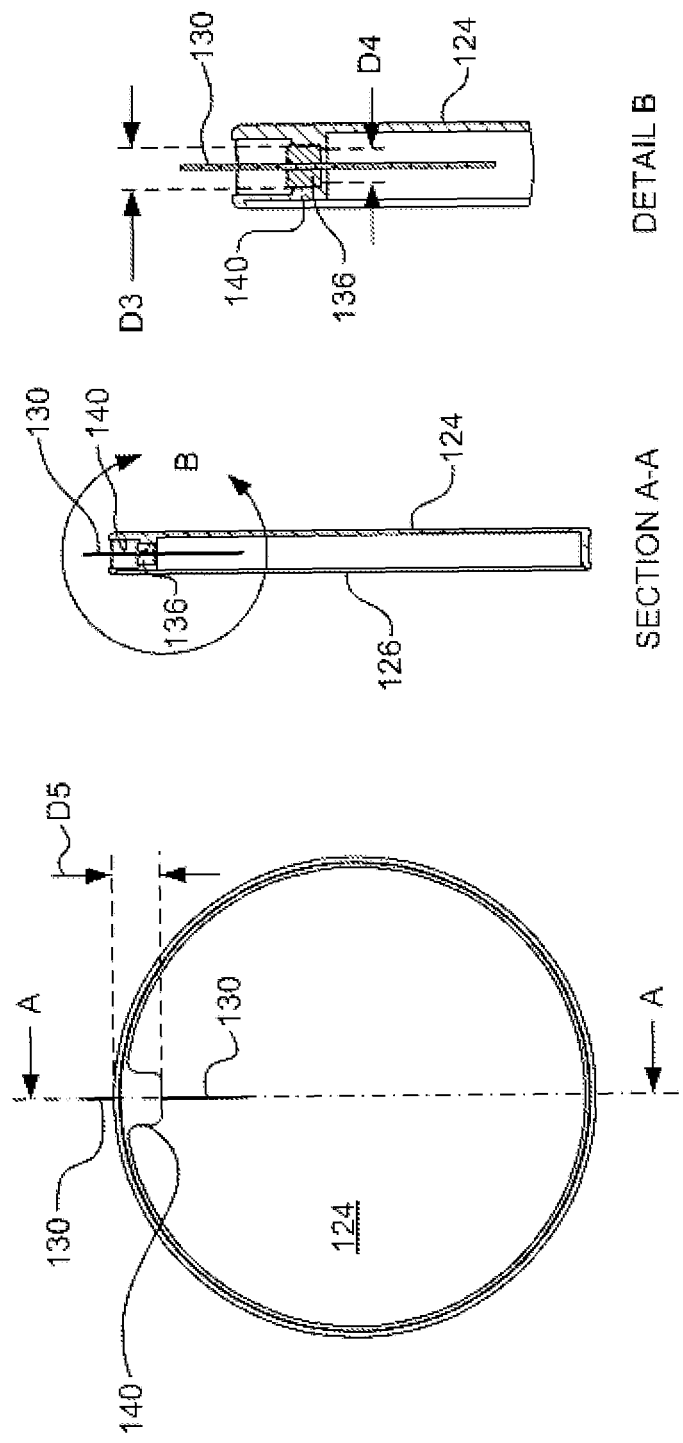

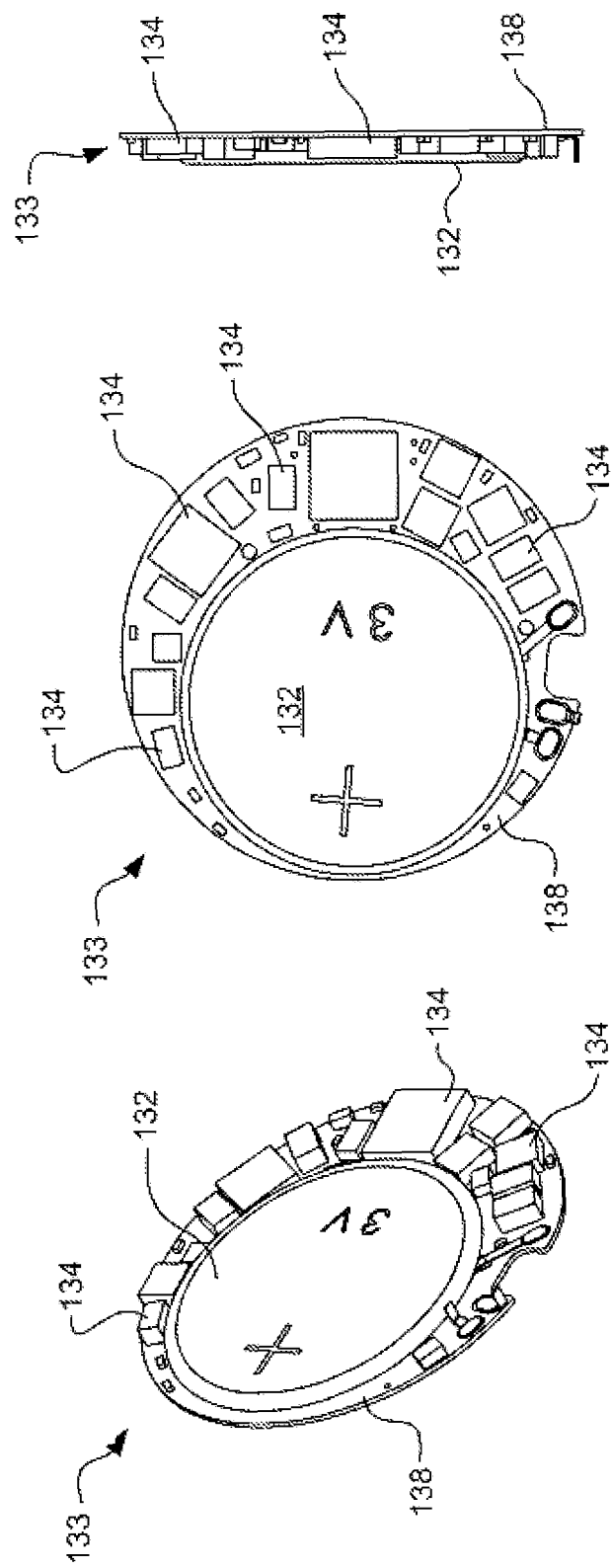

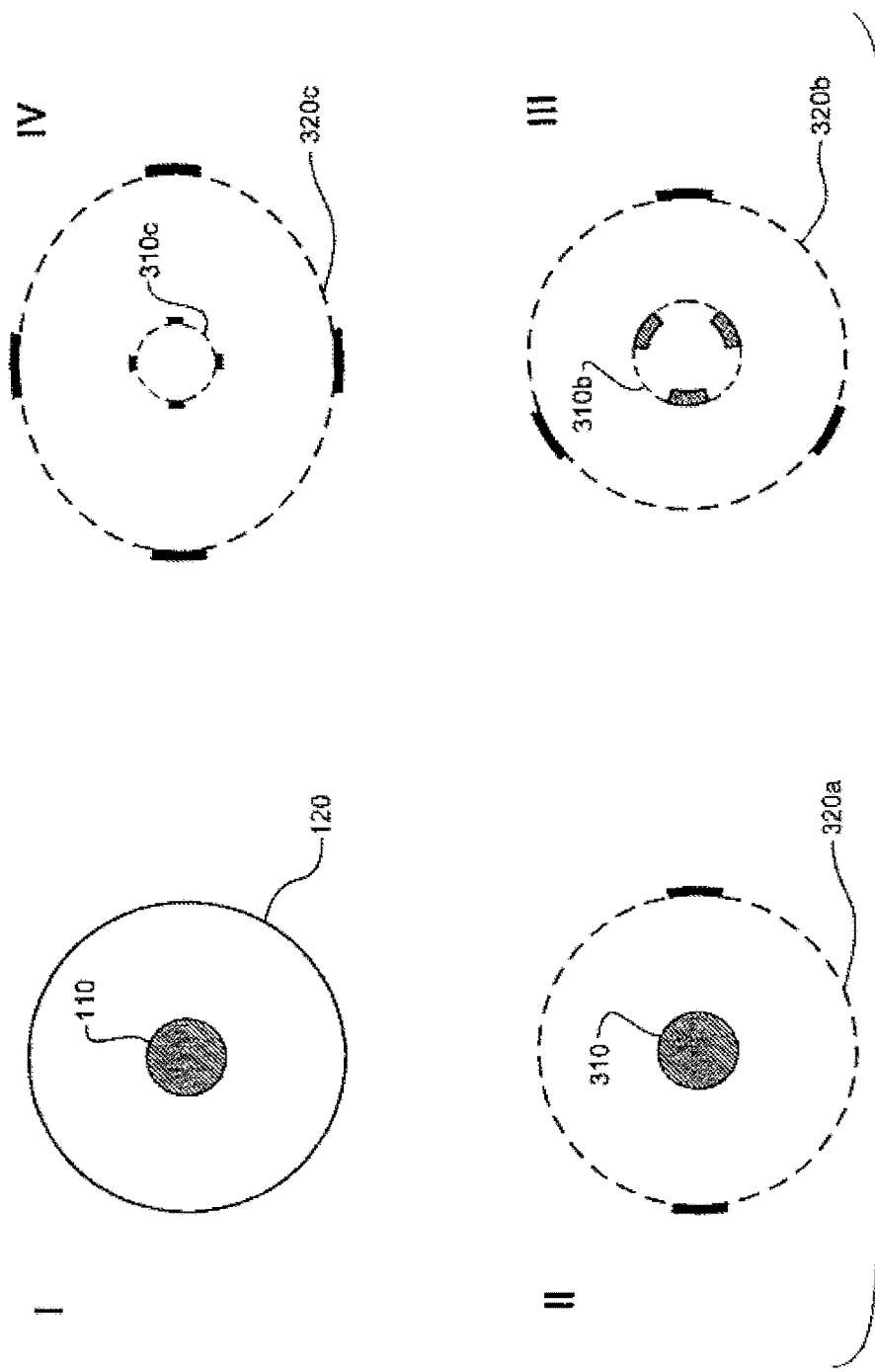

IMPLANTABLE ELECTROACUPUNCTURE SYSTEM AND METHOD FOR TREATING PARKINSON'S DISEASE AND ESSENTIAL TREMOR THROUGH APPLICATION OF STIMULUI AT OR NEAR AN ACUPOINT ON THE CHOREA LINE

RELATED APPLICATIONS

This application is a Continuation-In-Part (CIP) of U.S. patent application Ser. No. 13/765,572, filed Feb. 12, 2013, which application is a CIP of U.S. patent application Ser. No. 13/630,522, filed Sep. 28, 2012, which applications (including the provisional applications referenced in their first paragraphs) are incorporated herein by reference.

BACKGROUND

Parkinson's disease (PD) is a common disorder that affects the brain's ability to control movement. More than one million people in North America have been diagnosed with PD, most of whom are over 60 years old. Parkinson's progressively worsens over time, although the rate of worsening varies greatly from person to person. Many people with the disease who are treated may be able to live years without serious disability. A number of treatments are available to help manage the symptoms and improve a person's quality of life. However, there is no cure for the disease at this time.

Essential tremor is a disorder of the nervous system that causes a rhythmic shaking or tremor. It can affect almost any part of the body but the trembling most often occurs in the hands and is especially bothersome during the attempt to do simple tasks like drinking from a glass or writing with a pencil. Essential tremor may also affect one's head, voice, arms, or legs. While it is not the same as Parkinson's disease, the tremor of Parkinson's disease resembles essential tremor and some of the same treatments, e.g., deep brain stimulation, are given to both disorders.

The cause of Parkinson's disease is unknown. (Note, throughout this application, "Parkinson's disease" may be shortened to just "Parkinson's".) Normally, certain nerve cells called neurons in the brain make a chemical called dopamine that helps control movement. In people with Parkinson's, these neurons slowly degenerate and lose their ability to produce dopamine. As a result, the symptoms of Parkinson's develop gradually and tend to become more severe over time. It is not well understood how and why these neurons stop working correctly.

The signs and symptoms of Parkinson's can be divided into motor and nonmotor. Motor symptoms are those that affect movement of the body. These are the most obvious symptoms of the disease. The main motor symptoms of Parkinson's are tremor, slowness of movement (called "bradykinesia"), stiffness ("rigidity"), and poor balance ("postural instability" or "gait impairment"). These symptoms are usually mild in the early stages of the disease.

Symptoms typically start on one side of the body and spread to the other side over a few years. As symptoms worsen, a patient may have difficulty walking, talking, and performing daily tasks. While the symptoms typically progress slowly, progression varies from person to person. During the early stages of the disease, symptoms can be managed fairly well with drugs.

The symptom of tremor caused by Parkinson's disease is the most noticeable when a person is at rest. The tremor of early Parkinson's is intermittent and may not be noticeable to others. Tremor usually becomes noticeable one hand at a time, spreading to the second hand over a period of a few years.

The symptom of bradykinesia or slowness of movement eventually affects everyone with the disease. It may result in feelings of lack of coordination, weakness, and fatigue. In the arms, bradykinesia can cause difficulty with daily tasks like buttoning clothing and clicking a computer mouse. It may cause a patient to drag his legs when walking, take shorter shuffling steps, or have a feeling of unsteadiness. A person may also have difficulty standing from a chair or getting out of a car.

The symptom of rigidity causes stiffened movement of the arms, legs, or body. It usually begins on the same side of the body as the other early symptoms and similarly to other symptoms, eventually affects the other side.

The symptom of postural instability deals with the failure of automatic reflexes that help a person remain balanced when standing and walking. The loss of balance or falling usually does not occur until late in the progression of the disease. However, postural instability may require a patient to use assistance of another person or a wheelchair to get around. Postural instability early in the disease state is suggestive of another Parkinsonism syndrome and not Parkinson's disease.

The nonmotor symptoms of the disease are those unrelated to movement. Many nonmotor symptoms affect a person's mood, the five senses, and the ability to think. Problems with thinking and problems with memory commonly occur in the disease and can range from mild to severe. Some studies indicate that forty percent or more of patients are affected with these problems over the long term. Common cognitive symptoms include difficulty making decisions or multi-tasking, remembering events, and judging distances.

Psychosis, or the disorder of thinking that causes a person to lose touch with reality, occurs in twenty to forty percent of people treated with medication for Parkinson's disease. The underlying cause of psychosis is poorly understood, although many medications used to treat Parkinson's can cause psychosis as a side effect, particularly in a person who already has cognitive impairment. Visual hallucinations are the most common symptoms of psychosis in Parkinson's and they often become more frequent and severe as the disease progresses.

In addition to psychosis, mood disorders such as depression, anxiety, and loss of motivation are common in people with Parkinson's. All of these conditions decrease a person's quality of life and worsen motor symptoms.

People with Parkinson's disease also have sleep disorders and excessive daytime sleepiness affects about 75 percent of people with the disease. It may be worsened by the medications used to treat Parkinson's. Some simply feel sleepy while others experience sudden and unintentional sleeping periods during the daytime.

There can be some autonomic dysfunction in Parkinson's with symptoms such as low blood pressure after standing up, constipation, difficulty swallowing, abnormal sweating, urinary leakage, and libido dysfunction.

One's sense of smell is commonly lost by people with Parkinson's. It usually happens early in the course of the disease even before many of the more familiar symptoms appear and it often goes unnoticed by the patient.

Painful sensations are also reported by Parkinson's patients—by more than 40 percent of patients. The pain can be piercing or stabbing, burning or tingling, and may be felt in several places or only in specific areas of the body including the face, abdomen, genitals, and joints. In general, painful sensations are experienced in the same body parts as the motor symptoms, and may be more prominent as medications wear off.

The diagnosis of Parkinson's disease relies upon the patient's signs and symptoms and not a blood or imaging test. Generally, bradykinesia (or slow movement) must be present to make a diagnosis and one of the two other primary symptoms: tremor and rigidity. Other factors supportive of the diagnosis are: symptoms began on one side of the body; the tremor occurs as the person's limb is resting; and the symptoms can be controlled with Parkinson's medication.

An alternative approach for treating Parkinson's disease, and/or Essential Tremor and a host of other physiological conditions, illnesses, deficiencies and disorders is acupuncture, which includes traditional acupuncture and acupressure. Acupuncture has been practiced in Eastern civilizations (principally in China, but also in other Asian countries) for at least 2500 years. It is still practiced today throughout many parts of the world, including the United States and Europe. A good summary of the history of acupuncture, and its potential applications may be found in Cheung, et al., "*The Mechanism of Acupuncture Therapy and Clinical Case Studies*", (Taylor & Francis, publisher) (2001) ISBN 0-415-27254-8, hereafter referred to as "Cheung, *Mechanism of Acupuncture,* 2001." The Forward, as well as Chapters 1-3, 5, 7, 8, 12 and 13 of Cheung, *Mechanism of Acupuncture,* 2001, are incorporated herein by reference.

Despite the practice in Eastern countries for over 2500 years, it was not until President Richard Nixon visited China (in 1972) that acupuncture began to be accepted in the West, such as the United States and Europe. One of the reporters who accompanied Nixon during his visit to China, James Reston, from the New York Times, received acupuncture in China for post-operative pain after undergoing an emergency appendectomy under standard anesthesia. Reston experienced pain relief from the acupuncture and wrote about it in The New York Times. In 1973 the American Internal Revenue Service allowed acupuncture to be deducted as a medical expense. Following Nixon's visit to China, and as immigrants began flowing from China to Western countries, the demand for acupuncture increased steadily. Today, acupuncture therapy is viewed by many as a viable alternative form of medical treatment, alongside Western therapies. Moreover, acupuncture treatment is now covered, at least in part, by most insurance carriers. Further, payment for acupuncture services consumes a not insignificant portion of healthcare expenditures in the U.S. and Europe. See, generally, Cheung, *Mechanism of Acupuncture,* 2001, vii.

Acupuncture is an alternative medicine that treats patients by insertion and manipulation of needles in the body at selected points. See, Novak, Patricia D. et al (1995). Dorland's Pocket Medical Dictionary (25th ed.), Philadelphia: (W.B. Saunders Publisher), ISBN 0-7216-5738-9. The locations where the acupuncture needles are inserted are referred to herein as "acupuncture points" or simply just "acupoints". The location of acupoints in the human body has been developed over thousands of years of acupuncture practice, and maps showing the location of acupoints in the human body are readily available in acupuncture books or online. For example, see, "Acupuncture Points Map," found online at: http://www.acupuncturehealing.org/acupuncture-points-map.html. Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Tongli. The same acupoint may be identified by others by the name followed with a letter/number combination placed in parenthesis, e.g., Tongli (HT5). Alternatively, the acupoint may be identified by its letter/number combination followed by its name, e.g., HT5 (Tongli). The first letter(s) typically refers to a body organ or meridian, or other tissue location associated with, or affected by, that acupoint. However, usually only the letter(s), not the name of the body organ or tissue location, is used in referring to the acupoint, but not always. Thus, for example, the acupoint GV20 is the same as acupoint Governing Vessel 20 which is the same as GV-20 which is the same as GV 20 which is the same as Baihui. For purposes of this patent application, unless specifically stated otherwise, all references to acupoints that use the same name, or the same first letter and the same number, and regardless of slight differences in second letters and formatting, are intended to refer to the same acupoint.

An excellent reference book that identifies all of the traditional acupoints within the human body is *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations* 2008"). The Table of Contents, Forward (page v-vi) and General Guidelines for Acupuncture Point Locations (pages 1-21), as well as pages 188 and 213 (which illustrate with particularity the location of acupoints GB34 and GV20, respectively) of the WHO Standard Acupuncture Point Locations 2008 are incorporated herein by reference.

While many in the scientific and medical community are highly critical of the historical roots upon which acupuncture has developed, (e.g., claiming that the existence of meridians, qi, yin and yang, and the like have no scientific basis), see, e.g., http://en.wikipedia.org/wiki/Acupuncture, few can refute the vast amount of successful clinical and other data, accumulated over centuries of acupuncture practice, that shows needle manipulation applied at certain acupoints is quite effective.

The World Health Organization and the United States' National Institutes of Health (NIH) have stated that acupuncture can be effective in the treatment of neurological conditions and pain. Reports from the USA's National Center for Complementary and Alternative Medicine (NC-CAM), the American Medical Association (AMA) and various USA government reports have studied and commented on the efficacy of acupuncture. There is general agreement that acupuncture is safe when administered by well-trained practitioners using sterile needles, but not on its efficacy as a medical procedure.

An early critic of acupuncture, Felix Mann, who was the author of the first comprehensive English language acupuncture textbook, *Acupuncture: The Ancient Chinese Art of Healing*, stated that "The traditional acupuncture points are no more real than the black spots a drunkard sees in front of his eyes." Mann compared the meridians to the meridians of longitude used in geography—an imaginary human construct. See, Mann, Felix (2000). *Reinventing acupuncture: a new concept of ancient medicine*. Oxford: Butterworth-Heinemann. pp. 14; 31. ISBN 0-7506-4857-0. Mann attempted to combine his medical knowledge with that of Chinese theory. In spite of his protestations about the theory, however, he apparently believed there must be something to it, because he was fascinated by it and trained many people in the West with the parts of it he borrowed. He also wrote many books on this subject. His legacy is that there is now a college in London and a system of needling that is known as "Medical Acupuncture". Today this college trains doctors and Western medical professionals only.

For purposes of this patent application, the arguments for and against acupuncture are interesting, but not that relevant. What is important is that a body of literature exists that identifies several acupoints within the human body that, rightly or wrongly, have been identified as having an influence on, or are otherwise somehow related to, the treatment of Parkinson's disease and Essential Tremor. With respect to these acupoints, the facts speak for themselves. Either these points do or do not affect the conditions, deficiencies or illnesses with which they have been linked. The problem lies in trying to ascertain what is fact from what is fiction. This problem is made more difficult when conducting research on this topic because the insertion of needles, and the manipulation of the needles once inserted, is more of an art than a science, and results from such research become highly subjective. What is needed is a much more regimented approach for doing acupuncture research.

It should also be noted that other medical research, not associated with acupuncture research, has over the years identified nerves and other locations throughout a patient's body where the application of electrical stimulation produces a beneficial effect for the patient. Indeed, the entire field of neurostimulation deals with identifying locations in the body where electrical stimulation can be applied in order to provide a therapeutic effect for a patient. For purposes of this patent application, such known locations within the body are treated essentially the same as acupoints—they provide a "target" location where electrical stimulation may be applied to achieve a beneficial result, whether that beneficial result is to reduce cholesterol or triglyceride levels, to reduce excess body fat, to treat cardiovascular disease, to treat mental illness, or to address some other issue associated with a disease or condition of the patient.

Returning to the discussion regarding acupuncture, some have proposed applying moderate electrical stimulation at selected acupuncture points through needles that have been inserted at those points. See, e.g., http://en.wikipedia.org/wiki/Electroacupuncture. Such electrical stimulation is known as electroacupuncture (EA). According to Acupuncture Today, a trade journal for acupuncturists: "Electroacupuncture is quite similar to traditional acupuncture in that the same points are stimulated during treatment. As with traditional acupuncture, needles are inserted on specific points along the body. The needles are then attached using small clips to an external device that generates continuous electric pulses. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 30 minutes at a time." "Acupuncture Today: Electroacupuncture". 2004 Feb. 1 (retrieved on-line 2006 Aug. 9 at http://www.acupuncturetoday.com/abc/electroacupuncture.php).

U.S. Pat. No. 7,155,279, issued to Whitehurst et al., discloses use of an implantable miniature neurostimulator, referred to as a "microstimulator," that can be implanted for stimulation of the vagus nerve and used as a therapy (alongside drugs) for movement disorders.

Other patents of Whitehurst et al. teach the use of this small, microstimulator, placed in other body tissue locations, including within an opening extending through the skull into the brain, for the treatment of a wide variety of conditions, disorders and diseases. See, e.g., U.S. Pat. No. 6,735,475 (headache and facial pain); U.S. Pat. No. 7,003,352 (epilepsy by brain stimulation); U.S. Pat. No. 7,013,177 (pain by brain stimulation); U.S. Pat. No. 6,950,707 (obesity and eating disorders); U.S. Pat. No. 7,292,890 (Vagus nerve stimulation); U.S. Pat. No. 7,203,548 (cavernous nerve stimulation); U.S. Pat. No. 7,440,806 (diabetes by brain stimulation); U.S. Pat. No. 7,610,100 (osteoarthritis); and U.S. Pat. No. 7,657,316 (headache by stimulating motor cortex of brain).

Techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,393,324; 6,006,134; 7,171,266; 7,171,266 and 7,373,204. The methods and devices disclosed in these patents, however, typically utilize (i) large implantable stimulators having long leads that must be tunneled through tissue over an extended distance to reach the desired stimulation site, (ii) external devices that must interface with implanted electrodes via percutaneous leads or wires passing through the skin, or (iii) inefficient and power-consuming wireless transmission schemes. Such devices and methods are still far too invasive, or are ineffective, and thus subject to the same limitations and concerns as are the previously described electrical stimulation devices.

One area used to treat Parkinson's disease and related conditions is a location on the scalp known alternatively as the chorea tremor area, the chorea trembling area or the chorea line. The chorea line is a line that begins about a centimeter anterior to acupoint GV20 and follows parallel to the Motor Area Line. The chorea line is located parallel with and about 1.5 cm anterior to the Motor Area Line.

The chorea line might also be described as MS6 (where "MS" is derived from "micro-system" and "scalp point"), which is a line on the scalp, or as the line drawn from GV21 to GB5.

The acupoint, Baihui, is also designated by DU20 and GV20. Both "GV" and "DU" stand for the Governing Vessel meridian. GV20 is located on the head at the midpoint of the connecting line between the auricular apices. It is also about 4.5 inches superior to the anterior hairline on the anterior median line.

The present disclosure herein describes a device which treats through electrical stimulation the area of the scalp known alternatively as the chorea line, MS6, DU20 or GV20. In one instance, such device is suitable or treating all of the tissue proximate the chorea line simultaneously. In another instance, such device treats tissue at discrete points along the chorea line either simultaneously or individually.

From the above, it is seen that there is a need in the art for a less invasive device and technique for electroacupuncture stimulation of acupoints that does not require the continual use of needles inserted through the skin, or long insulated wires implanted or inserted into blood vessels, for the purposes of improving the symptoms of or slowing the progression of Parkinson's disease and Essential Tremor.

SUMMARY

One characterization of the invention described herein is an Implantable ElectroAcupuncture System (IEAS) that treats Parkinson's disease and Essential Tremor through application of electroacupuncture (EA) stimulation pulses applied at a specified tissue location(s) of a patient. A key component of such IEAS is an implantable electroacupuncture (EA) device. The EA device has a small, hermetically-sealed housing containing a primary power source, pulse generation circuitry powered by the primary power source, and a sensor that wirelessly senses operating commands generated external to the housing. The pulse generation circuitry generates stimulation pulses in accordance with a specified stimulation regimen as controlled, at least in part, by the operating commands sensed through the sensor. The EA device further includes a plurality of electrode arrays (where an electrode array comprises an array of n conductive contacts electrically joined together to function jointly as one electrode, where n is an integer of from 1 to 24) on the outside of the EA device housing that are electrically coupled to the pulse generation circuitry on the inside of the EA device housing. There is at least one cathodic electrode array and one anodic electrode array. Such electrical coupling occurs through at least one feed-through terminal passing through a wall of the hermetically-sealed housing. Stimulation pulses generated by the pulse generation circuitry inside of the EA device housing are directed to the plurality of electrode arrays on the outside of the EA housing so as to flow between the anodic electrode(s) and the cathodic electrode(s). As the stimulation pulses flow between these anodic and cathodic electrode(s), they are applied at the specified tissue location(s) through the plurality of electrode arrays in accordance with the specified stimulation regimen. The specified stimulation regimen defines how often a stimulation session (a stimulation session comprises a stream or burst of stimulation pulses applied to the specified tissue location(s) over a prescribed period of time) is applied to the patient, and the duration of each stimulation session. Moreover, the stimulation regimen requires that the stimulation session be applied at a very low duty cycle. More particularly, if the stimulation session has a duration of T3 minutes and occurs at a rate of once every T4 minutes, then the duty cycle, or the ratio of T3/T4, cannot be greater than 0.05. The specified tissue location(s) whereat EA stimulation pulses are applied comprises at least one of acupoints GV20 and GB34.

Another characterization of the invention described herein is an Implantable ElectroAcupuncture System (IEAS) for treating Parkinson's disease and Essential Tremor. Such IEAS includes (a) an implantable electroacupuncture (EA) device housing having a maximum linear dimension of no more than 25 mm in a first plane, and a maximum height of no more 2.5 mm in a second plane orthogonal to the first plane; (b) a primary battery within the EA device housing having an internal impedance of no less than about 5 ohms; (c) pulse generation circuitry within the EA device housing and powered by the primary battery that generates stimulation pulses during a stimulation session; (d) control circuitry within the EA device housing and powered by the primary battery that controls the frequency of the stimulation sessions to occur no more than once every T4 minutes, and that further controls the duration of each stimulation session to last no longer than T3 minutes, where the ratio of T3/T4 is no greater than 0.05; (e) sensor circuitry within the EA device housing and coupled to the control circuitry that is responsive to the presence of a control command generated external to the EA device housing, which control command when received by the control circuitry sets the times T3 and T4 to appropriate values; and (f) a plurality of electrodes located outside of the EA device housing that are electrically coupled to the pulse generation circuitry within the EA device housing. The plurality of electrodes are positioned to lie at or near a target tissue location(s) belonging to the group of target tissue locations comprising at least one of acupoints GV20 or GB34.

Yet another characterization of the invention described herein is a method for treating Parkinson's disease and Essential Tremor in a patient. The method includes: (a) implanting an electroacupuncture (EA) device in the patient below the patient's skin at or near at least one specified target tissue location; (b) enabling the EA device to generate stimulation sessions at a duty cycle that is less than or equal to 0.05, wherein each stimulation session comprises a series of stimulation pulses, and wherein the duty cycle is the ratio of T3/T4, where T3 is the duration of each stimulation session, and T4 is the time or duration between stimulation sessions; and (c) delivering the stimulation pulses of each stimulation session to at least one specified target tissue location through a plurality of electrode arrays electrically connected to the EA device. Here, an electrode array comprises an array of n conductive contacts electrically joined together to function jointly as one electrode, where n is an integer. The at least one specified target tissue location at which the stimulation pulses are applied in this method is selected from the group of target tissue locations comprising at least one of acupoints GV20 or GB34.

A further characterization of the invention described herein is a method of treating Parkinson's disease and Essential Tremor in a patient using a small implantable electroacupuncture device (IEAD). Such IEAD is powered by a small disc primary battery having a specified nominal output voltage of about 3 volts and having an internal impedance of at least 5 ohms. The IEAD is configured, using electronic circuitry within the IEAD, to generate stimulation pulses in accordance with a specified stimulation regimen. These stimulation pulses are applied at a selected tissue location of the patient through at least two electrodes located outside of the housing of the IEAD. The method comprises: (a) implanting the IEAD below the skin surface of the patient at or near a target tissue location selected from the group of target tissue locations comprising at least one of acupoints GV20 or GB34; and (b) enabling the IEAD to provide stimulation pulses in accordance with a stimulation regimen that provides a stimulation session of duration T3 minutes at a rate of once every T4 minutes, where the ratio of T3/T4 is no greater than 0.05, and wherein T3 is at least 10 minutes and no greater than 60 minutes.

The invention described herein may additionally be characterized as a method of assembling an implantable electroacupuncture device (IEAD) in a small, thin, hermetically-sealed, housing having a maximum linear dimension in a first plane of no more than 25 mm and a maximum linear dimension in a second plane orthogonal to the first plane of no more than 2.5 mm. Such housing has at least one feed-through pin assembly radially passing through a wall of the thin housing that isolates the feed-through pin assembly from high temperatures and residual weld stresses that occur when the thin housing is welded shut to hermetically-seal its contents. The IEAD thus assembled is particularly adapted for use in treating Parkinson's disease or Essential Tremor of a patient. The method of assembling comprises the steps of:
  (a) forming a thin housing having a bottom case and a top cover plate, the top cover plate being adapted to fit over the bottom case, the bottom case having a maximum linear dimension of no more than 25 mm;
  (b) forming a recess in a wall of the housing;

(c) placing a feed-through assembly within the recess so that a feed-through pin of the feed-through assembly electrically passes through a wall of the recess at a location that is separated from where the wall of the housing is designed to contact the top cover plate; and (d) welding the top cover plate to the bottom case around a perimeter of the bottom case, thereby hermetically sealing the bottom case and top case together.

Yet another characterization of the invention described herein is an Implantable ElectroAcupuncture System (IEAS) for treating Parkinson's disease or Essential Tremor. Such IEAS includes (a) at least one external component, and (b) a small, thin implantable component having a maximum linear dimension in a first plane of less than 25 mm, and a maximum linear dimension in a second plane orthogonal to the first plan of no more than 2.5 mm.

An additional characterization of the invention described herein is an Implantable ElectroAcupuncture System (IEAS) for treating Parkinson's disease or Essential Tremor. Such IEAS includes (a) an implantable electroacupuncture (EA) device housing having a maximum linear dimension of no more than 25 mm in a first plane, and a maximum height of no more 2.5 mm in a second plane orthogonal to the first plane; (b) a primary battery within the EA device housing having an internal impedance of no less than about 5 ohms; (c) pulse generation circuitry within the EA device housing and powered by the primary battery that generates stimulation pulses during a stimulation session; (d) control circuitry within the EA device housing and powered by the primary battery that controls the frequency of the stimulation sessions; (e) sensor circuitry within the EA device housing and coupled to the control circuitry that is responsive to the presence of a control command generated external to the EA device housing, which control command when received by the control circuitry sets the times T3 and T4 to appropriate values; (f) a conduit extending externally from the EA housing; (g) one or more lead is carried within the conduit, which one or more leads are in electrical communication with the pulse generation circuitry within the EA housing. The conduit is defined as a tubular wall having one or more openings formed through the wall, each opening is positioned at or near a target tissue location belonging to the group of acupoints along the chorea line, the one or more leads each include an electrode, with one electrode positioned adjacent each opening; wherein the electrodes provide electrical stimulation from the pulse generation circuitry to the tissue proximate the openings. In one instance, an electrode is also formed on the exterior of the EA device housing, wherein the electrode on the housing serves as an anode and each of the one or more electrodes in the conduit serves as a cathode.

An additional characterization of the invention described herein is an Implantable ElectroAcupuncture System (IEAS) for treating Parkinson's disease or Essential Tremor. Such IEAS includes (a) an implantable electroacupuncture (EA) device housing having a maximum linear dimension of no more than 25 mm in a first plane, and a maximum height of no more 2.5 mm in a second plane orthogonal to the first plane; (b) a primary battery within the EA device housing having an internal impedance of no less than about 5 ohms; (c) pulse generation circuitry within the EA device housing and powered by the primary battery that generates stimulation pulses during a stimulation session; (d) control circuitry within the EA device housing and powered by the primary battery that controls the frequency of the stimulation sessions; (e) sensor circuitry within the EA device housing and coupled to the control circuitry that is responsive to the presence of a control command generated external to the EA device housing, which control command when received by the control circuitry sets the times T3 and T4 to appropriate values; (f) a conduit extending externally from the EA housing; (g) a plurality of leads carried within the conduit, each of the leads are in electrical communication with the pulse generation circuitry within the EA housing whereby each of the leads are independently controllable by the control circuitry. The conduit is defined as a tubular wall having a plurality of openings formed through the wall, each opening is positioned at or near a target tissue location belonging to the group of acupoints along the chorea line, each lead includes an electrode, such that one electrode is positioned at each opening to provide electrical stimulation to the tissue adjacent the opening.

An additional characterization of the invention described herein is an Implantable ElectroAcupuncture System (IEAS) for treating Parkinson's disease or Essential Tremor. Such IEAS includes (a) an implantable electroacupuncture (EA) device housing having a maximum linear dimension of no more than 25 mm in a first plane, and a maximum height of no more 2.5 mm in a second plane orthogonal to the first plane; (b) a primary battery within the EA device housing having an internal impedance of no less than about 5 ohms; (c) pulse generation circuitry within the EA device housing and powered by the primary battery that generates stimulation pulses during a stimulation session; (d) control circuitry within the EA device housing and powered by the primary battery that controls the frequency of the stimulation sessions; (e) sensor circuitry within the EA device housing and coupled to the control circuitry that is responsive to the presence of a control command generated external to the EA device housing, which control command when received by the control circuitry sets the times T3 and T4 to appropriate values; (f) a conduit extending externally from the EA housing; (g) a plurality of leads is carried within the conduit, each of the leads are in electrical communication with the pulse generation circuitry within the EA housing whereby each of the leads are independently controllable by the control circuitry. The conduit is defined as a tubular wall having a plurality of openings formed through the wall, each opening is positioned at intervals along the conduit, such as spaced 1 mm to 10 mm apart, each lead includes an electrode such that an electrode is positioned at each opening, the control circuitry is configured to send pulses to each electrode individually. The control circuitry is designed such that the electrodes can receive pulses either individually or in combination. When the control circuitry sends a pulse to a single electrode, the electrode will provide electrical stimulation to the tissue located adjacent the opening in the conduit where the given electrode is located. In instances where the openings in the conduit do not align with target tissue locations, electrical fields emanating from two or more electrodes of the EA device may be combined or superimposed so as to create a virtual electrode whose virtual position may be finely adjusted to be precisely at the desired location along the conduit. Alternatively, the openings may be spaced at irregular intervals along the length of the conduit such that the openings are proximate the target tissue locations.

An additional characterization of the invention described herein is an Implantable ElectroAcupuncture System (IEAS) for treating Parkinson's disease or Essential Tremor. Such IEAS includes (a) an implantable electroacupuncture (EA) device housing having a maximum linear dimension of no more than 25 mm in a first plane, and a maximum height of no more 2.5 mm in a second plane orthogonal to the first plane; (b) a primary battery within the EA device housing having an internal impedance of no less than about 5 ohms; (c) pulse generation circuitry within the EA device housing and powered by the primary battery that generates stimulation pulses during a stimulation session; (d) control circuitry within the EA device housing and powered by the primary battery that controls the frequency of the stimulation sessions; (e) sensor circuitry within the EA device housing and coupled to the control circuitry that is responsive to the presence of a control command generated external to the EA device housing, which control command when received by the control circuitry sets the times T3 and T4 to appropriate values; (f) a conduit extending externally from the EA housing; (g) a lead is carried within the conduit, which lead is in electrical communication with the pulse generation circuitry within the EA housing. The conduit is defined as a tubular wall having one or more openings formed through the wall, each opening is positioned at or near a target tissue location belonging to the group of acupoints along the chorea line. The lead includes a plurality of electrodes positioned along the length of the lead such that an electrode is positioned at each opening, and a given electrode stimulates the tissue adjacent the corresponding opening. In one instance, the openings are evenly spaced along the length of the conduit. In another instance, the openings are spaced along the conduit at uneven intervals, and are spaced such that the openings align with one of the target tissue locations on the chorea line.

An additional characterization of the invention described herein is an Implantable ElectroAcupuncture System (IEAS) for treating Parkinson's disease or Essential Tremor. Such IEAS includes (a) an implantable electroacupuncture (EA) device housing having a maximum linear dimension of no more than 25 mm in a first plane, and a maximum height of no more 2.5 mm in a second plane orthogonal to the first plane; (b) a primary battery within the EA device housing having an internal impedance of no less than about 5 ohms; (c) pulse generation circuitry within the EA device housing and powered by the primary battery that generates stimulation pulses during a stimulation session; (d) control circuitry within the EA device housing and powered by the primary battery that controls the frequency of the stimulation sessions; (e) sensor circuitry within the EA device housing and coupled to the control circuitry that is responsive to the presence of a control command generated external to the EA device housing, which control command when received by the control circuitry sets the times T3 and T4 to appropriate values; (f) a conduit extending externally from the EA housing; (g) a lead is carried within the conduit, which lead is in electrical communication with the pulse generation circuitry within the EA housing. The conduit is defined as a tubular wall having one or more openings formed through the wall, each opening is positioned at or near a target tissue location belonging to the group of acupoints along the chorea line, the lead includes a plurality of electrodes which stimulate the tissue adjacent each opening. One electrode is positioned at each opening. The size of each opening is chosen to determine the intensity of treatment at each opening, with the intensity of the electrical stimulation increasing as the size of the opening increases. The spacing of the openings is either at regular intervals, or at irregular intervals such that the openings are positioned adjacent the acupoints along the chorea line.

As used herein, "lead" refers to a length of wire sufficient for communicating electricity between the circuitry in the device housing and an electrode. As used herein, "electrode" is a portion of the lead which communicates electrical stimulation to the tissue. In some instances the lead is covered by a sheath except at the electrode, in other instances the lead is a bare wire running the length of the conduit with the electrode defined by the portion of the lead which is adjacent an opening in the conduit. Use of a sheath is advantageous when multiple leads are housed in the conduit.

In one preferred embodiment, the external component comprises an electromagnetic field generator. As used herein, the term "electromagnetic field" encompasses radio frequency fields, magnetic fields, light emissions, or combinations thereof.

The implantable component includes a housing made of a bottom part and a top part that are welded together to create an hermetically-sealed, closed container. At least one feed-through terminal passes through a portion of a wall of the top part or bottom part. This terminal allows electrical connection to be made between the inside of the closed container and a location on the outside of the closed container. Electronic circuitry, including a power source, is included on the inside of the closed container that, when enabled, generates stimulation pulses during a stimulation session that has a duration of T3 minutes. The electronic circuitry also generates a new stimulation session at a rate of once every T4 minutes. The ratio of T3/T4, or the duty cycle of the stimulation sessions, is maintained at a very low value of no greater than 0.05. The stimulation pulses are coupled to the at least one feed-through terminal, where they are connected to a plurality of electrodes/arrays located on an outside surface of the closed housing. The stimulation pulses contained in the stimulation sessions are thus made available to stimulate body tissue in contact with or near the plurality of electrodes/arrays on the outside of the closed housing.

Further included on the inside of the closed container is a sensor adapted to sense the presence or absence of an electromagnetic field. Also included on the inside of the closed container is a power source that provides operating power for the electronic circuitry.

In operation, the external component modulates an electromagnetic field which, when sensed by the sensor inside of the closed container, conveys information to the electronic circuitry inside of the closed housing that controls when and how long the stimulation sessions are applied through the plurality of electrodes/arrays. Once this information is received by the electronic circuitry, the external component can be removed and the implantable component of the IEAS will carry out the stimulation regimen until the power source is depleted or new information is received by the electronic circuitry, whichever occurs first.

BRIEF DESCRIPTION OF THE DRAWINGS

The above and other aspects, features and advantages of the invention will be more apparent from the following more particular description thereof, presented in conjunction with the following drawings. These drawings illustrate various embodiments of the principles described herein and are part of the specification. The illustrated embodiments are merely examples and do not limit the scope of the disclosure.

FIG. 2 shows a plan view of one surface of the IEAD housing illustrated in FIG. 1.

FIG. 2A shows a side view of the IEAD housing illustrated in FIG. 1.

FIG. 3 shows a plan view of the other side, indicated as the "Back Side," of the IEAD housing or case illustrated in FIG. 1.

FIG. 3A is a sectional view of the IEAD of FIG. 3 taken along the line A-A of FIG. 3.

FIG. 5 is a plan view of the empty IEAD housing shown in FIG. 4.

FIG. 5A depicts a sectional view of the IEAD housing of FIG. 5 taken along the section line A-A of FIG. 5.

FIG. 5B shows an enlarged view or detail of the portion of FIG. 5A that is encircled with the line B.

FIG. 6 is a perspective view of an electronic assembly, including a battery, that is adapted to fit inside of the empty housing of FIG. 4 and FIG. 5.

FIGS. 6A and 6B show a plan view and side view, respectively, of the electronic assembly shown in FIG. 6.

FIG. 7A schematically illustrates a few alternative electrode configurations that may be used with the invention.

Figure 1:
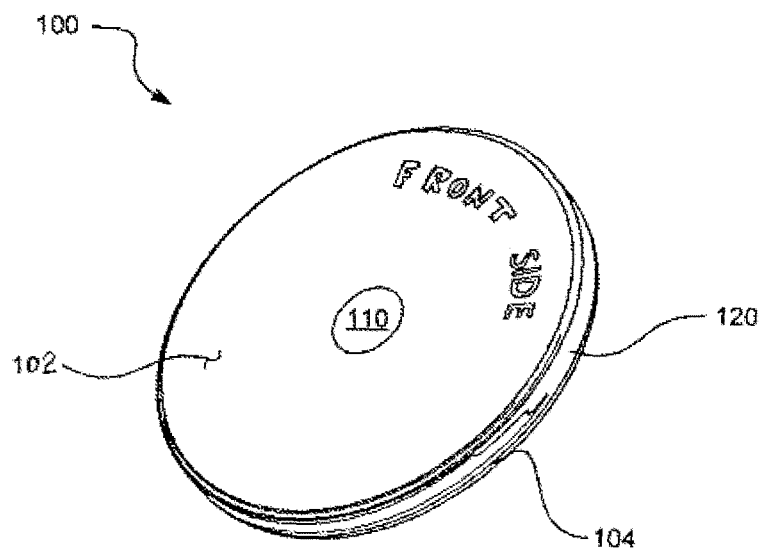
FIG. 1 is a perspective view of an Implantable Electroacupuncture Device (IEAD) made in accordance with the teachings presented herein.

Appendix A, found in Applicant's previously-filed grandparent patent application Ser. No. 13/630,522, filed Sep. 28, 2012 (hereafter the "'522 application"), illustrates some examples of alternate symmetrical electrode configurations that may be used with an IEAD of the type described herein.

Appendix B, also found in the '522 application, illustrates a few examples of non-symmetrical electrode configurations that may be used with an IEAD made in accordance with the teachings herein.

Appendix C, likewise found in the '522 application, shows an example of the code used in the micro-controller IC (e.g., U2 in FIG. 14) to control the basic operation and programming of the IEAD, e.g., to Turn the IEAD ON/OFF, adjust the amplitude of the stimulus pulse, and the like, using only an external magnet as an external communication element.

Appendix D, found in the '522 application, contains selected pages from the WHO Standard Acupuncture Point Locations 2008 reference book, referenced earlier herein.

Appendix E, found in the '522 application, contains illustrations of alternate case shapes that may be used with an IEAD of the type described herein.

Appendices A, B, C, D and E, found in the '522 application Applicant's previously-filed patent application Ser. No. 13/630,522, filed Sep. 28, 2012, are incorporated by reference herein.

Throughout the drawings and appendices, identical reference numbers designate similar, but not necessarily identical, elements.

DETAILED DESCRIPTION

Overview

Disclosed and claimed herein is an implantable, self-contained, leadless electroacupuncture (EA) device having at least two electrode contacts (also referred to as "electrodes") mounted on the surface of its housing. In some embodiments, these electrodes may be grouped together to form an electrode array. The EA device disclosed herein is adapted to treat Parkinson's disease or Essential Tremor in a patient. In one preferred embodiment, the electrodes on the surface of the EA device include a central cathode electrode on one side of the housing, and an annular anode electrode that surrounds the cathode. In another preferred embodiment, the anode annular electrode is a ring electrode placed around the perimeter edge of a coin-shaped housing.

A preferred application for an EA device made in accordance with the teachings presented herein is to treat Parkinson's disease or Essential Tremor. Thus, the description that follows describes in much more detail an EA device that is especially suited to be used to treat Parkinson's disease or Essential Tremor. However, it is to be understood that the invention is not limited to treating only Parkinson's disease or Essential Tremor.

Definitions

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular.

"Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−1.15 mm (0.05×23 mm=1.15 mm).

"Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

As explained in more detail below, a feature of the invention recognizes that an electroacupuncture modulation scheme need not be continuous, thereby allowing the implanted EA device to use a small, high density, power source to provide such non-continuous EA modulation. (Here, it should be noted that "EA modulation," as that phrase is used herein, is the application of electrical stimulation pulses, at low intensities, low frequencies and low duty cycles, to at least one of the target stimulation sites, e.g., an acupuncture site that has been identified as affecting a particular condition, e.g., Parkinson's disease and/or Essential Tremor.) As a result, the EA device can be very small. And, because the electrodes form an integral part of the housing of the EA device, the EA device may thus be implanted directly at (or very near to) the desired target tissue location, e.g., the target stimulation site, such as the target acupoint.

In summary, and as explained more fully below in conjunction with the description of the treatment method for treating Parkinson's and/or Essential Tremor, the basic approach of EA stimulation includes: (1) identify an acupoint(s) or other target stimulation site that may be used to treat or mediate the particular illness, condition or deficiency that has manifest itself in the patient, e.g., Parkinson's disease and/or Essential Tremor; (2) implant an EA device, made as described herein, so that its electrodes are located to be near or on the identified acupoint(s) or other target stimulation site; (3) apply EA modulation, having a low intensity, low frequency, and low duty cycle through the electrode(s) of the EA device so that electrical stimulation pulses flow through the tissue at the target stimulation site following a prescribed stimulation regimen over several weeks or months or years. At any time during this EA stimulation regimen, the patient's illness, condition or deficiency may be evaluated and, as necessary, the parameters of the EA modulation applied during the EA stimulation regimen may be adjusted or "tweaked" in order to improve the results obtained from the EA modulation.

Conditions Treated

Parkinson's disease (PD) is a common disorder that affects the brain's ability to control movement. Parkinson's progressively worsens over time, although the rate of worsening condition varies greatly from person to person. Many people with the disease who are treated may be able to live years without serious disability. A number of treatments are available to help manage the symptoms and improve a person's quality of life. However, there is no cure for the disease at this time.

The severity of Parkinson's is generally measured by the Unified Parkinson's Disease Rating Scale (UPDRS). The UPDRS has four categories: (I) Mentation, Behavior and Mood; (II) Activities of Daily Living; (III) Motor Examination; (4) Complications of Therapy. The third category, motor, was created largely from the Webster Scale, which was previously the most commonly used scale. The higher the score, the more severe the Parkinson's.

Many complications arise from drugs, such as dyskinesia and dystonia. Thus, the current scale attempts to account for the affect on the patient of using drugs for treatment. Furthermore, drugs become less effective over time in Parkinson's patients.

The Modified Hoehn and Yahr Staging Scale categorizes a patient's disease state in terms of stages, ranging from zero to 5. Stage zero means there are no signs of the disease. Stage 1 means there is unilateral disease. Stage 1.5 means there is unilateral plus axial involvement. Stage 2 means there is bilateral disease, without impairment of balance. Stage 2.5 means there is mild bilateral disease, with recovery on pull test. Stage 3 means there is mild to moderate bilateral disease, some postural instability and physical independence. Stage 4 means there is severe disability, but the patient is still able to walk or stand unassisted. The final stage, stage 5, means that the patient is wheelchair bound or bedridden unless aided.

Essential tremor is a disorder of the nervous system that causes a rhythmic shaking or tremor. It can affect almost any part of the body but the trembling most often occurs in the hands and is especially bothersome during the attempt to do simple tasks like drinking from a glass or writing with a pencil. Essential tremor may also affect one's head, voice, arms, or legs. While it is not the same as Parkinson's disease, the tremor of Parkinson's disease resembles essential tremor and some of the same treatments, e.g., deep brain stimulation, are given to both disorders.

In three clinical studies authored by mostly the same group of authors, there were two acupoints in common—LR3 and GB34—and the successful lowering of the average patient UPDRS score was achieved by some significant measure. See, Jung, J C, Kim K H, Park Y C, et al. [The study on the effect of acupuncture on UPDRS and heart rate variability in the patients with idiopathic Parkinson's disease]. J Korean Acupunct Moxibust Soc 2006; 23: 143-153 (in Korean with English translation) (hereafter, "Jung 2006"); Park Y C, Chang D I, Lee Y H, Park D S. [The study on the effect of acupuncture treatment in patients with idiopathic Parkinson's disease]. J Korean Acupunct Moxibust Soc 2007; 24: 43-54 (in Korean with English translation) (hereafter, "Park 2007"); Kang M K, Lee S H, Hong J M, Park S M, Kang J W, Park H J, Lim S, Chang D I, Lee Y H. [Effect of Electroacupuncture on Patients with Idiopathic Parkinson's Disease]. J Korean Acupunct Moxibust Soc 2004; 21; 5:59-68 (in Korean) (hereafter, "Kang 2004").

In addition, that main group of authors showed in experimental Parkinson's rats that manual acupuncture at GB34 and LR3 significantly improved the motor deficit. See, Park, H. J., Lim, S., Joo, W. S., Yin, C. S., Lee, H. S., Lee, H. J., . . . & Chung, J. H. (2003). Acupuncture prevents 6-hydroxydopamine-induced neuronal death in the nigrostriatal dopaminergic system in the rat Parkinson's disease model. *Experimental neurology*, 180(1), 93-98 (Park 2003").

In two of the three aforementioned studies, manual acupuncture was performed at acupoints GB34 and at LR3 (and at ST36 in one of the studies). In the third study, electroacupuncture was performed at GB34 and LR3. Over a course of four weeks, with acupuncture or EA for fifteen minute sessions twice a week, patients saw about eight to thirty percent reductions in their baseline UPDRS score. See, Jung 2006, Park 2007, Kang 2004. Applicant believes greater reductions can be brought about over longer stimulation sessions (i.e., 30 minute sessions) and over time.

For a study utilizing both body and scalp acupoints including GB34 with success, see, Chang, X. H., Zhang, L. Z., & Li, Y. J. (2008). Observation on therapeutic effect of acupuncture combined with medicine on Parkinson disease]. *Zhongguo zhen jiu=Chinese acupuncture & moxibustion*, 28(9), 645 (hereafter, "Chang 2008").

While the mechanism of action is not known, there are a number of theories that give credence to the efficacious results seen in certain acupuncture studies. The mechanism of action in stimulation at GB34 is likely to involve the following areas of the brain: the putamen and the primary motor cortex. In an MRI study utilizing three groups—an over placebo (or control) group, a verum acupuncture group, and a cover placebo group (nonpenetrating needle group)—the putamen and primary motor cortex were activated when patients with Parkinson's disease received acupuncture treatment at acupoint GB34 and the activations were correlated with improved motor function. See, Chae, Y., Lee, H., Kim, H., Kim, C. H., Chang, D. I., Kim, K. M., & Park, H. J. (2009). Parsing brain activity associated with acupuncture treatment in Parkinson's diseases. *Movement Disorders*, 24(12), 1794-1802 (hereafter, "Chae 2009"). In addition, expectations towards acupuncture modality elicited activation over the anterior cingulated gyrus, the superior frontal gyrus, and the superior temporal gyrus. The comparison of the covert placebo group to the overt placebo group allowed this deduction. See, Chae 2009.

In another MRI study of the brain during acupuncture at GB34, in healthy people, showed that electroacupuncture stimulation at the left GB34 specifically activated the right putamen, caudate body, claustrum, thalamus, cerebellum, as well as the left caudate body, ventral lateral thalamus, and cerebellum—all of which are related to motor function. See, Na, B. J., Jahng, G. H., Park, S. U., Jung, W. S., Moon, S. K., Park, J. M., & Bae, H. S. (2009). An fMRI study of neuronal specificity of an acupoint: electroacupuncture stimulation of Yanglingquan (GB34) and its sham point. *Neuroscience letters*, 464(1), 1-5 (hereafter, "Na 2009"). Electroacupuncture at the sham point, on the other hand, specifically activated the right BA6, BA8, BA40, BA44, thalamus, as well as the left thalamus and cerebellum. See, Nah 2009. Electroacupuncture at GB34 and its sham point induced specific neuronal responses—and EA at GB34 appears to be more related to motor function than EA at its sham point, even though the sham point is located very close by, suggestive of acupoint specificity.

The mechanism of action may involve the inhibition of the motor system. In a study on healthy people, acupuncture at GB34 was compared to sham acupuncture using a non-penetrating needle. See, Zunhammer, M., Eichhammer, P., Franz, J., Hajak, G., & Busch, V. (2012). Effects of acupuncture needle penetration on motor system excitability, *Neurophysiologie Clinique/Clinical Neurophysiology* (hereafter, "Zunhammer 2012"). Verum acupuncture compared to sham acupuncture significantly increased resting motor threshold. Thus, it may be that acupuncture at GB34 is reducing the excitability of the motor system in Parkinson's patients.

In another study on healthy people, acupuncture at GB34 and a control group who rested demonstrated that acupuncture at GB34 is effective for decreasing muscle fatigue (during an arm flexion test). See, Kwon Hoyoung, Kim Jeonghwan (2008). The effects of Yanggnungch'on (G34) acupuncture on the muscle. Journal of Meridian & Acupoint Society: Society of Meridian & Acupoint; 25(2): 115-123. Korean with English abstract (hereafter, "Kwon 2008").

The mechanism of action may involve the regulation of dopamine content in the striatum. In a study of experimental hemi-parkinsonism rats before and after EA at LR3, SP6, ST36, and GB34 on the lesioned side, EA treatment could elevate the dopamine level of the lesioned side striatum and prevent $D_2$ receptor up-regulation. See, Un, Y., & Lin, X. (2000). Comparative study of $D_2$ receptors and dopamine content in striatum before and after electro-acupuncture treatment in rats. *Chinese medical journal*, 113(5), 408 (hereafter, "Lin 2000").

For an example of the enhanced survival of dopaminergic neurons in the experimental rat Parkinson's brain after acupuncture (at two limb acupoints in Park's study and at one scalp and one back acupoint in Lian's study), see, Park 2003, Liang 2002. See also, Liu, X. Y., Zhou, H. F., Pan, Y. L., Liang, X. B., Niu, D. B. Xue, B., & Wang, X. M. (2004). Electro-acupuncture stimulation protects dopaminergic neurons from inflammation-mediated damage in medial forebrain bundle-transected rats. *Experimental neurology*, 189 (1), 189-196 (hereafter, "Liu 2004").

Last, the mechanism of action for acupuncture stimulation of scalp acupoints (specifically at GV20 and a single back acupoint GV14) may stem from the collaboration of its anti-inflammatory and neurotrophic actions. The neuroprotective effect of high frequency stimulation in experimental Parkinson's rats (or "medial forebrain bundle-transected rats") has been demonstrated in two studies conducted by Han for which a single scalp acupoint and a single back acupoint are utilized alone. See, Liang 2002, Liu 2004.

Locations Stimulated and Stimulation Paradigms/Regimens

The acupoints for stimulation for purposes of this application are at least one acupoint located in a limb of the patient, and one acupoint located in the scalp. The limb acupoint is GB34. The acupoint GB34, which might be referred to as "Yanglingquan" or its different spellings (e.g., "Yanglingchuan"), is located on the leg in the fossa anterior and inferior to the head of the fibula. See FIG. 1D. See also, *WHO Standard Acupuncture Point Locations* 2008, page 188, incorporated herein by reference.

For purposes of this patent application, the scalp stimulation location has been identified as acupoint GV20. Its location is shown in FIGS. 1A, 1B and 1C. The acupoint GV20 is also sometimes referred to as Baihui, and may also be designated as either DU20 or GV20. Both "GV" and "DU" stand for the Governing Vessel meridian. GV20 is located on the head at the midpoint of the connecting line between the auricular apices. It is also about 4.5 inches superior to the anterior hairline on the anterior median line. See also, *WHO Standard Acupuncture Point Locations* 2008, page 213, incorporated herein by reference.

For stimulation at either the limb (GB34) or at the scalp (GV20), the stimulation parameters are the same.

The stimulation duration should be between fifteen minutes and sixty minutes, and, the rate of stimulation occurrence should be between once daily and once every other week. While the acupuncture studies on which Applicant relies for the utilization of the limb acupoint GB34 apply acupuncture with a short duration of fifteen minutes, see, Kang 2004, Park 2007, Jung 2006, Applicant believes the history and experience of acupuncture science support a longer stimulation duration.

The electrical parameters of stimulation should require a frequency between 1 Hz and 15 Hz for a low frequency setting, and between 100 Hz and 120 Hz for a high frequency setting. Thus, there are two different settings for the frequency: a high and a low frequency setting. The amplitude of the stimulus pulses should be between 1 mA and 15 mA, and the pulse width of the stimulation pulses should be about 0.5 ms.

For an example of successful scalp electroacupuncture stimulation utilizing low frequency, see e.g., Shun 2003. For an example of successful high frequency scalp electroacupuncture stimulation or high frequency limb electroacupuncture stimulation, respectively, see e.g., Yong 2009, Liang 2002, Liu 2004; and Kang 2004. Manual acupuncture at the identified limb point also brings about positive results in Parkinson's. See e.g., Park 2007, Jung 2006.

In a study performed by Yong et al, patients with high baseline UPDRS motor scores saw reductions of about 24%. See, Yong 2009. The stimulation parameters, however, were not manual acupuncture like most successful acupuncture studies known to Applicant for treatment of Parkinson's disease or Essential Tremor, but high frequency electroacupuncture. The stimulation parameters were 100 Hz, 2-4 mA, with continuous wave, 30 minutes daily for six days a week over a course of five weeks. However, EA was performed only at one or two of the five stimulated acupoints depending upon the symptoms.

In a study performed by J S Han, who is well known for his work in pain, high frequency EA was utilized in rats and improvement in lesions were measured. In a partially lesioned rat model of Parkinson's disease, high frequency stimulation brought about a stop in the degeneration of dopaminergic neurons in the substantia nigra and upregulating the levels of brain-derived neurotrophic factor (BDNF) mRNA in the subfields of the ventral midbrain. In this rat study, low frequency stimulation did not similarly affect the brain. See, Liang, X. B., Liu, X. Y Li, F. Q., Luo, Y., Lu, J., Zhang, W. M., . . . & Han, J. S. (2002). Long-term high-frequency electro-acupuncture stimulation prevents neuronal degeneration and up-regulates BDNF mRNA in the substantia nigra and ventral tegmental area following medal forebrain bundle axotomy. *Molecular brain research,* 108 (1), 51-59 (hereafter, "Liang 2002").

The pulse width Applicant has selected to use is between 0.5 ms and 2 ms in consideration of Applicant's understanding of neuromodulation and the recruitment of fibers and in consideration of at least one study for which a long pulse width of 2 ms was utilized. See, Shun 2003.

The rate of occurrence of the stimulation sessions should be as frequently as daily and as infrequent as once weekly. For examples of improvement of Parkinson's symptoms from acupuncture stimulation applied at acupoints GV20 or GB34 administered twice weekly, see, Kang 2004, Park 2007, Jung 2006. For an example of more frequent or daily stimulation and success, see, Wang, S., Cai, Y. Y., Shang, Y. J., & Jin-Rong, L. (2006). Effects of head point-through-point electroacupuncture on SOD and LPO in the patient of Parkinson's disease. *Zhongguo Zhen Jiu,* 26(4), 240-242 (hereafter, "Wang 2006"); Chang 2008.

Specific Example

A specific example of the invention will next be described in combination with a more detailed explanation of the figures. Although one specific example is being described, there are many variations of it that are generally referred to in the description of the specific example as "embodiments".

The EA device of this specific example being described comprises an implantable, coin-shaped, self-contained, symmetrical, leadless electroacupuncture (EA) device having at least two electrode contacts mounted on the surface of its housing. In one preferred embodiment, the electrodes include a central cathode electrode on a front side of the housing, and an annular anode electrode that surrounds the cathode. In another preferred embodiment, the anode annular electrode is a ring electrode placed around the perimeter edge of the coin-shaped housing.

The EA device is leadless. This means there are no leads or electrodes at the distal end of leads (common with most implantable electrical stimulators) that have to be positioned and anchored at a desired stimulation site. Also, because there are no leads, no tunneling through body tissue is required in order to provide a path for the leads to return and be connected to a tissue stimulator (also common with most electrical stimulators).

The EA device is adapted to be implanted through a very small incision, e.g., less than 2-3 cm in length, directly adjacent to a selected acupuncture site ("acupoint") known to moderate or affect body weight, fat or lipid profile.

The EA device is relatively easy to implant. Also, most embodiments are symmetrical. This means that there is no way that it can be implanted incorrectly. The basic implant procedure involves cutting an incision, forming an implant pocket, and sliding the device in place through the incision.

Only minor, local anesthesia need be used. No major or significant complications are envisioned for the implant procedure. The EA device can also be easily and quickly explanted, if needed.

The EA device is self-contained. It includes a primary battery to provide its operating power. It includes all of the circuitry it needs, in addition to the battery, to allow it to perform its intended function for several years. Once implanted, the patient will not even know it is there, except for a slight tingling that may be felt when the device is delivering stimulus pulses during a stimulation session. Also, once implanted, the patient can just forget about it. There are no complicated user instructions that must be followed. Just turn it on. No maintenance is needed. Moreover, should the patient want to disable the EA device, i.e., turn it OFF, or change stimulus intensity, he or she can easily do so using, e.g., an external magnet.

The EA device can operate for several years because it is designed to be very efficient. Stimulation pulses applied by the EA device at a selected acupoint through its electrodes formed on its case are applied at a very low duty cycle in accordance with a specified stimulation regimen. The stimulation regimen applies EA stimulation during a stimulation session that lasts at least 10 minutes, typically 30 minutes, and rarely longer than 70 minutes. These stimulation sessions, however, occur at a very low duty cycle. In one preferred treatment regimen, for example, a stimulation session having a duration of 60 minutes is applied to the patient just once every seven days. The stimulation regimen, and the selected acupoint at which the stimulation is applied, are designed and selected to provide efficient and effective EA stimulation for the treatment of Parkinson's disease or Essential Tremor.

The EA device is, compared to most implantable medical devices, relatively easy to manufacture and uses few components. This not only enhances the reliability of the device, but helps keep the manufacturing costs low, which in turn allows the device to be more affordable to the patient. One key feature included in the mechanical design of the EA device is the use of a radial feed-through assembly to connect the electrical circuitry inside of its housing to one of the electrodes on the outside of the housing. The design of this radial feed-through pin assembly greatly simplifies the manufacturing process. The process places the temperature sensitive hermetic bonds used in the assembly—the bond between a pin and an insulator and the bond between the insulator and the case wall—away from the perimeter of the housing as the housing is hermetically sealed at the perimeter with a high temperature laser welding process, thus preserving the integrity of the hermetic bonds that are part of the feed-through assembly.

In operation, the EA device is safe to use. There are no horrific failure modes that could occur. Because it operates at a very low duty cycle (i.e., it is OFF much, much more than it is ON), it generates little heat. Even when ON, the amount of heat it generates is not much, less than 1 mW, and is readily dissipated. Should a component or circuit inside of the EA device fail, the device will simply stop working. If needed, the EA device can then be easily explanted.

Another key feature included in the design of the EA device is the use of a commercially-available battery as its primary power source. Small, thin, disc-shaped batteries, also known as "coin cells," are quite common and readily available for use with most modern electronic devices. Such batteries come in many sizes, and use various configurations and materials. However, insofar as applicants are aware, such batteries have never been used in implantable medical devices previously. This is because their internal impedance is, or has always thought to have been, much too high for such batteries to be of practical use within an implantable medical device where power consumption must be carefully monitored and managed so that the device's battery will last as long as possible, and so that dips in the battery output voltage (caused by any sudden surge in instantaneous battery current) do not occur that could compromise the performance of the device. Furthermore, the energy requirements of other active implantable therapies are far greater than can be provided by such coin cells without frequent replacement.

The EA device of this specific example advantageously employs power-monitoring and power-managing circuits that prevent any sudden surges in battery instantaneous current, or the resulting drops in battery output voltage, from ever occurring, thereby allowing a whole family of commercially-available, very thin, high-output-impedance, relatively low capacity, small disc batteries (or "coin cells") to be used as the EA device's primary battery without compromising the EA device's performance. As a result, instead of specifying that the EA device's battery must have an high capacity, e.g., greater than 200 mAh, with an internal impedance of, e.g., less than 5 ohms, which would either require a thicker battery and/or preclude the use of commercially-available coin-cell batteries, the EA device of the present invention can readily employ a battery having a relatively low capacity, e.g., less than 60 mAh, and a high battery impedance, e.g., greater than 5 ohms.

Moreover, the power-monitoring, power-managing, as well as the pulse generation, and control circuits used within the EA device are relatively simple in design, and may be readily fashioned from commercially-available integrated circuits (IC's) or application-specific integrated circuits (ASIC's), supplemented with discrete components, as needed. In other words, the electronic circuits employed within the EA device need not be complex nor expensive, but are simple and inexpensive, thereby making it easier to manufacture the EA device and to provide it to patients at an affordable cost.

Mechanical Design

Figures 1A, 1B:
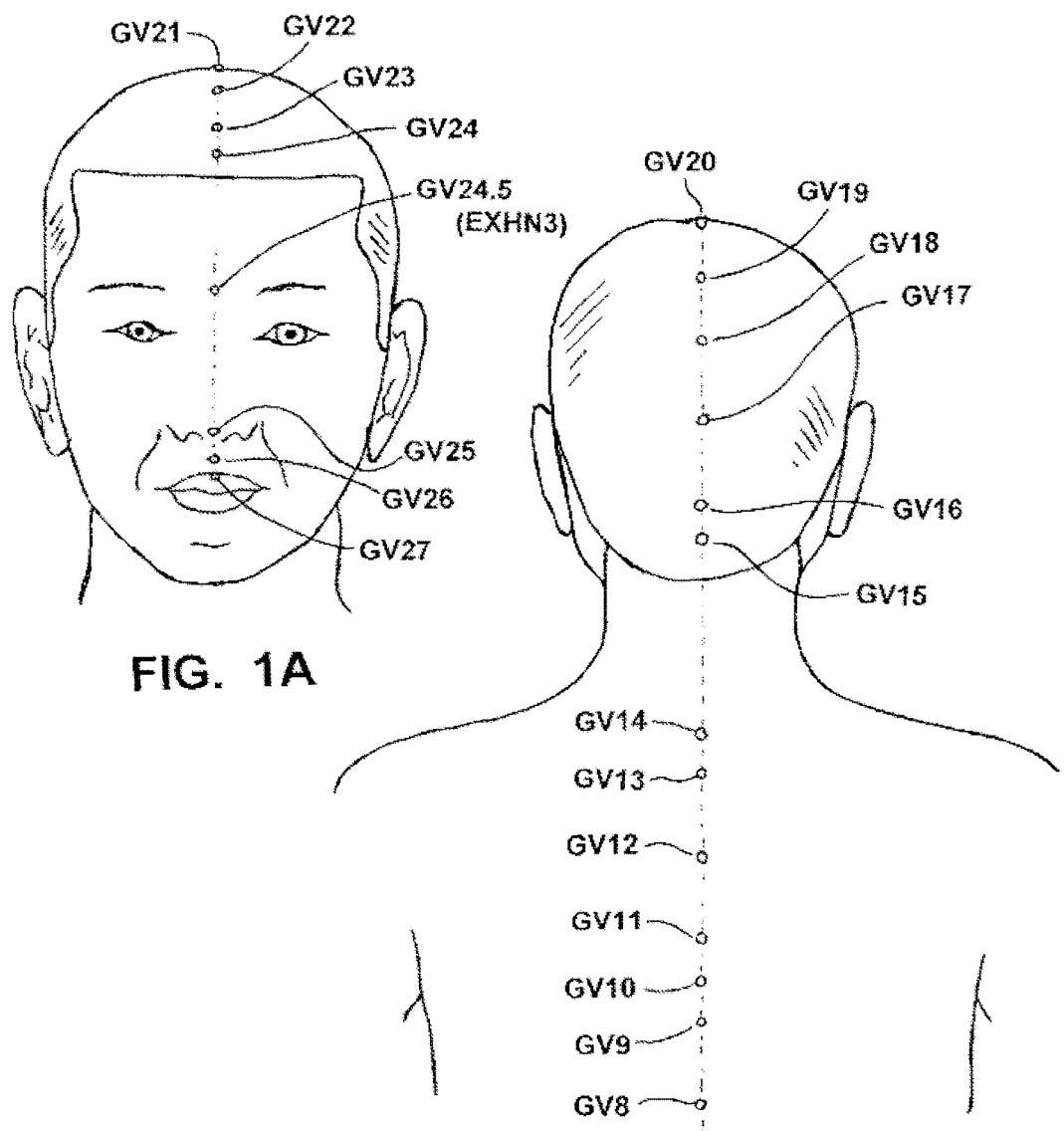
FIGS. 1A, 1B and 1C show front, back and side views of the head, respectively, and illustrate with particularity the location of acupoint GV20 or Baihui, one of the locations identified herein for implantation of the IEAD for the treatment of Parkinson's disease and Essential Tremor.
Figure 1C:
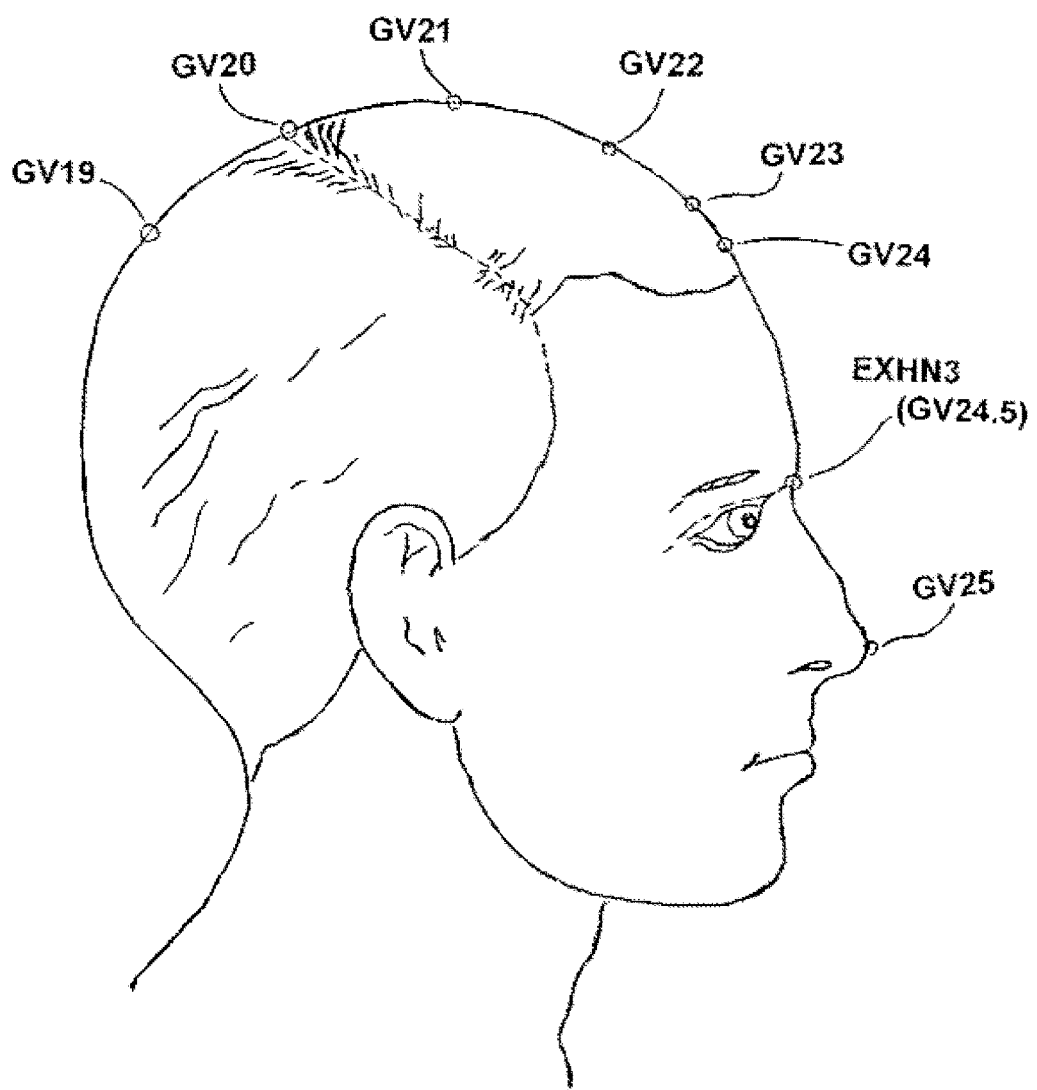
Figure 1D:
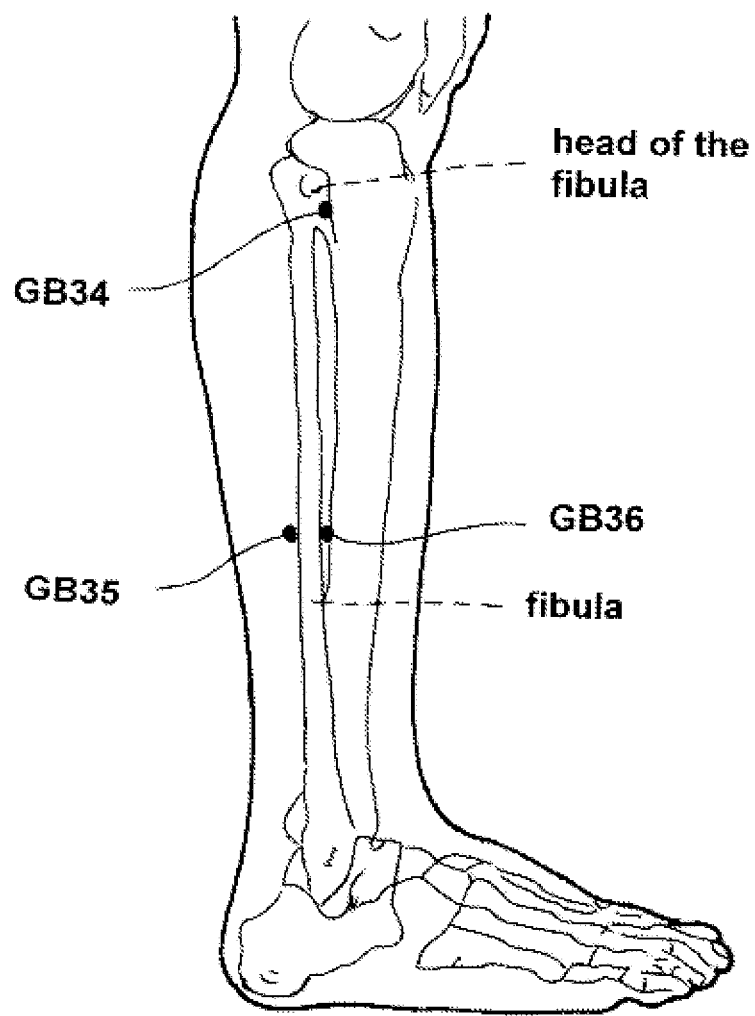
FIG. 1D shows the location of acupoint GB34 or Yanglingquan.

Turing first to FIG. 1, there is shown a perspective view of one preferred embodiment of an implantable electroacupuncture device (IEAD) 100 that may be used to treat Parkinson's disease and/or Essential Tremor in accordance with the teachings disclosed herein. The IEAD 100 may also sometimes be referred to as an implantable electroacupuncture stimulator (IEAS). As seen in FIG. 1, the IEAD 100 has the appearance of a disc or coin, having a front side 102, a back side 106 (not visible in FIG. 1) and an edge side 104.

As used herein, the "front" side of the IEAD 100 is the side that is positioned so as to face the target stimulation point (e.g., the desired acupoint) where EA is to be applied when the IEAD is implanted. The "back" side is the side opposite the front side and is the farthest away from the target stimulation point when the IEAD is implanted. The "edge" of the IEAD is the side that connects or joins the front side to the back side. In FIG. 1, the IEAD 100 is oriented to show the front side 102 and a portion of the edge side 104.

Many of the features associated with the mechanical design of the IEAD 100 shown in FIG. 1 are the subject of a prior U.S. Provisional Patent Application, entitled "Radial Feed-Through Packaging for An Implantable Electroacupuncture Device", Application No. 61/676,275, filed 26 Jul. 2012, which application is incorporated here by reference.

It should be noted here that throughout this application, the terms IEAD 100, IEAD housing 100, bottom case 124, can 124, or IEAD case 124, or similar terms, are used to describe the housing structure of the EA device. In some instances it may appear these terms are used interchangeably. However, the context should dictate what is meant by these terms. As the drawings illustrate, particularly FIG. 7, there is a bottom case 124 that comprises the "can" or "container" wherein the components of the IEAD 100 are first placed and assembled during manufacture of the IEAD 100. When all of the components are assembled and placed within the bottom case 124, a cover plate 122 is welded to the bottom case 124 to form the hermetically-sealed housing of the IEAD. The cathode electrode 110 is attached to the outside of the bottom case 124 (which is the front side 102 of the device), and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 7:
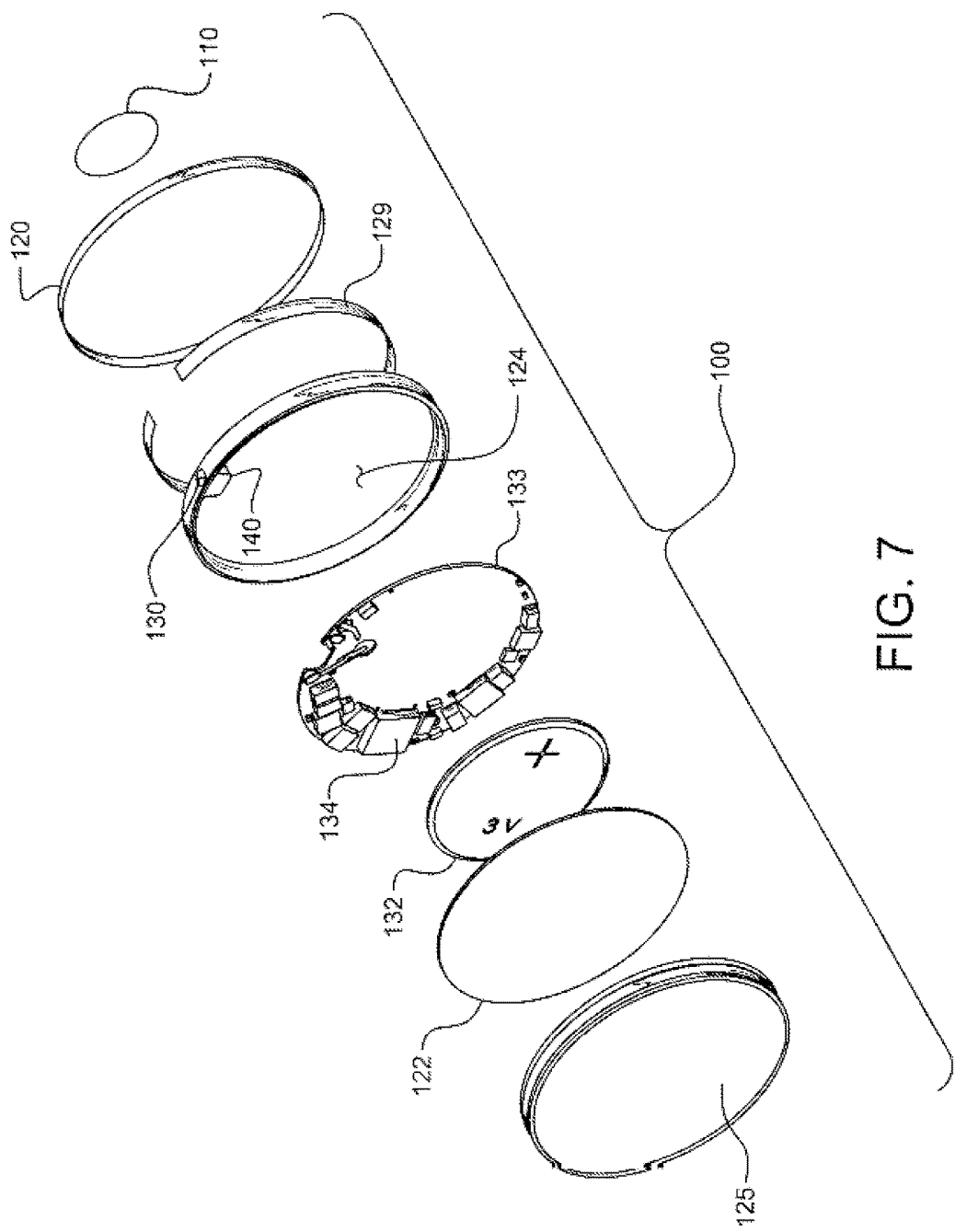
FIG. 7 is an exploded view of the IEAD assembly, illustrating its constituent parts.

The embodiment of the IEAD 100 shown in FIG. 1 utilizes two electrodes, a cathode electrode 110 that is centrally positioned on the front side 102 of the IEAD 100, and an anode electrode 120. The anode electrode 120 is a ring electrode that fits around the perimeter edge 104 of the IEAD 100. Not visible in FIG. 1, but which is described hereinafter in connection with the description of FIG. 7, is a layer of insulating material 129 that electrically insulates the anode ring electrode 120 from the perimeter edge 104 of the housing or case 124.

Not visible in FIG. 1, but a key feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 5, 5A, 5B and 7.

In contrast to the feed-through pin that establishes electrical contact with the anode electrode, electrical connection with the cathode electrode 110 is established simply by forming or attaching the cathode electrode 110 to the front surface 102 of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 7), except for the outside surface of the anode ring electrode 120 and the cathode electrode 110.

The advantage of using a central cathode electrode and a ring anode electrode is described in U.S. Provisional Patent Application No. 61/672,257, filed 6 Mar. 2012, entitled "Electrode Configuration for Implantable Electroacupuncture Device", which application is incorporated herein by reference. One significant advantage of this electrode configuration is that it is symmetrical. That is, when implanted, the surgeon or other medical personnel performing the implant procedure, need only assure that the cathode side of the IEAD 100, which (for the embodiment shown in FIGS. 1-7) is the front side of the device, facing the target tissue location that is to be stimulated.

In this regard, it should be noted that while the target stimulation point is generally identified by an "acupoint," which is typically shown in drawings and diagrams as residing on the surface of the skin, the surface of the skin is not the actual target stimulation point. Rather, whether such stimulation comprises manual manipulation of a needle inserted through the skin at the location on the skin surface identified as an "acupoint", or whether such stimulation comprises electrical stimulation applied through an electrical field oriented to cause stimulation current to flow through the tissue at a prescribed depth below the acupoint location on the skin surface, the actual target tissue point to be stimulated is located beneath the skin at a depth that varies depending on the particular acupoint location. When stimulation is applied at the target tissue point, such stimulation is effective at treating a selected condition of the patient, e.g., Parkinson's disease, because there is something in the tissue at that location, or near that location, such as a nerve, a tendon, a muscle, or other type of tissue, that responds to the applied stimulation in a manner that contributes favorably to the treatment of the condition experienced by the patient.

Figure 17A:
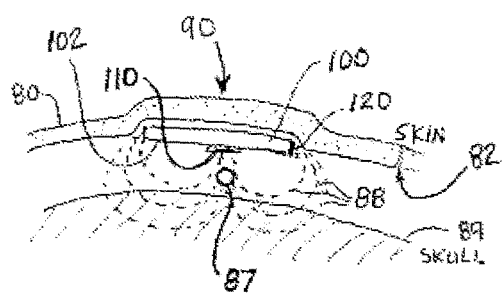
FIG. 17A illustrates one technique for implanting an IEAD under the skin in a location where a front surface of the IEAD faces inward toward a bone surface of the patient.
Figure 17B:
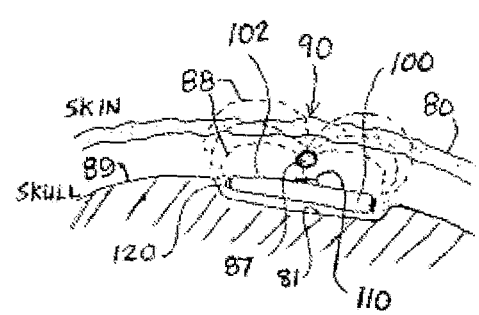
FIG. 17B depicts an alternative technique for implanting an IEAD in a pocket formed in a bone below a desired acupoint, with a front surface of the IEAD facing outward towards the skin.

For purposes of the present application, some of the target acupoints are located near a bone of the patient. When the bone is very close to the skin surface, the location of the bone may prevent deep tissue stimulation, and may even prevent or hamper implantation at a desired depth. This condition—of having a bone near the skin surface—is illustrated schematically in FIGS. 17A and 17B. As seen in these figures, the bone is shown generally as being right under the skin 80, with not much tissue separating the two. These two figures assume that the actual desired target stimulation point is below acupoint 90 at a nerve 87 (or some other tissue formation) between the underneath side of the skin 80 and the top surface of the bone 89. Hence, the challenge is to implant the IEAD 100 in a manner that provides effective EA stimulation at the desired target stimulation site, e.g., at the nerve 87 (or other target tissue formation) that resides beneath the acupoint 90. FIGS. 17A and 17B illustrate alternative methods for achieving this goal.

Shown in FIG. 17A is one alternative for implanting the IEAD 100 at an acupoint 90 located on the surface of the skin 80 above a bone 89, where the actual target stimulation point is a nerve 87, or some other tissue formation, that is located between the bone 89 and the underneath side of the skin 80. As shown in FIG. 17A, the IEAD 100 is implanted right under the skin with its front surface 102 facing down towards the target tissue location 87. This allows the electric fields (illustrated by the electric field gradient lines 88) generated by the IEAD 100 when EA stimulation pulses are to be generated to be most heavily concentrated at the target tissue stimulation site 87. These electric field gradient lines 88 are established between the two electrodes 110 and 120 of the IEAD. For the embodiment shown here, these two electrodes comprise a ring electrode 120, positioned around the perimeter edge of the IEAD housing, and a central electrode 110, positioned in the center of the front surface 102 of the IEAD housing. These gradient lines 88 are most concentrated right below the central electrode, which is where the target tissue location 87 resides. Hence, the magnitude of the electrical stimulation current will also be most concentrated at the target tissue location 87, which is the desired result.

FIG. 17B shows another alternative for implanting the IEAD 100 at the acupoint 90 located on the surface of the skin 80 above the bone 89, where the actual target stimulation point is a nerve 87, or some other tissue formation, that is located between the bone 89 and the underneath side of the skin 80. As shown in FIG. 17B, the IEAD 100 is implanted in a pocket 81 formed in the bone 89 at a location underneath the acupoint 90. In this instance, and as the elements are oriented in FIG. 17B, the front surface 102 of the IEAD 100 faces upwards towards the target tissue location 87. As with the implant configuration shown in FIG. 17A, this configuration also allows the electric fields (illustrated by the electric field gradient lines 88) that are generated by the IEAD 100 when EA stimulation pulses are generated to be most heavily concentrated at the target tissue stimulation site 87.

There are advantages and disadvantages associated with each of the two alternative implantation configurations shown in FIGS. 17A and 17B. Generally, the implantation procedure used to achieve the configuration shown in FIG. 17A is a simpler procedure with fewer risks. That is, all that need to be done by the surgeon to implant that EA device 100 as shown in FIG. 17A is to make an incision 82 in the skin 80 a short distance, e.g., 10-15 mm, away from the acupoint 90. This incision should be made parallel to the nerve 87 so as to minimize the risk of cutting the nerve 87. A slot is then formed at the incision by lifting the skin closest to the acupoint up at the incision and by carefully sliding the IEAD 100, with its front side 102 facing the bone, into the slot so that the center of the IEAD is located under the acupoint 90. Care is taken to assure that the nerve 87 resides below the front surface of the IEAD 100 as the IEAD is slid into position.

In contrast, if the implant configuration shown in FIG. 17B is to be used, then the implant procedure is somewhat more complicated with somewhat more risks. That is, to achieve the implant configuration shown in FIG. 17B, a sufficiently large incision must be made in the skin at the acupoint 90 to enable the skin 80 to be peeled or lifted away to expose the surface of the bone so that the cavity 81 may be formed in the bone 89. While doing this, care must be exercised to hold the nerve 87 (or other sensitive tissue areas) away from the cutting tools used to form the cavity 81. Once the cavity 81 is formed, the IEAD 100 is laid in the cavity, with its front surface facing upward, the nerve 87 (and other sensitive tissue areas) are carefully repositioned above the IEAD 100, and the skin is sewn or clamped to allow the incision to heal.

However, while the surgical procedure and attendant risks may be more complicated when the configuration of FIG. 17B is employed, the final results of the configuration of FIG. 17B may be more aesthetically pleasing to the patient than are achieved with the configuration of FIG. 17A. That is, given the shallow space between the skin and the bone at a desired acupoint, the implant configuration of FIG. 17A will likely result in a small hump or bump at the implant site, whereas the implant configuration of FIG. 17B should not exhibit such a small hump or bump.

Insofar as Applicant is aware at the present time, of the two implant configurations shown in FIGS. 17A and 17B, there is no theoretical performance advantage that one implant configuration provides over the other. That is, both implant configurations should perform equally well insofar as providing EA stimulation pulses at the desired target tissue location 87 is concerned.

Thus, which implant configuration is used will, in large part, be dictated by individual differences in patient anatomy, patient preference, and surgeon preferences and skill levels.

From the above, it is seen that one of the main advantages of using a symmetrical electrode configuration that includes a centrally located electrode surrounded by an annular electrode, as is used in the embodiment described in connection with FIGS. 1-7, is that the precise orientation of the IEAD 100 within its implant location is not important. So long as one electrode faces and is centered over (or under) the desired target location, and the other electrode surrounds the first electrode (e.g., as an annular electrode), a strong electric field gradient is created that is aligned with the desired target tissue location. This causes the EA stimulation current to flow at (or very near to) the target tissue location 87.

Turning next to FIG. 2, there is shown a plan view of the "front" side of the IEAD 100. As seen in FIG. 2, the cathode electrode 110 appears as a circular electrode, centered on the front side, having a diameter D1. The IEAD housing has a diameter D2 and an overall thickness or width W2. For the preferred embodiment shown in these figures, D1 is about 4 mm, D2 is about 23 mm and W2 is a little over 2 mm (2.2 mm).

FIG. 2A shows a side view of the IEAD 100. The ring anode electrode 120, best seen in FIG. 2A, has a width W1 of about 1.0 mm, or approximately ½ of the width W2 of the IEAD.

FIG. 3 shows a plan view of the "back" side of the IEAD 100. As will be evident from subsequent figure descriptions, e.g., FIGS. 5A and 5B, the back side of the IEAD 100 comprises a cover plate 122 that is welded in place once the bottom case 124 has all of the electronic circuitry, and other components, placed inside of the housing.

FIG. 3A is a sectional view of the IEAD 100 of FIG. 1 taken along the line A-A of FIG. 3. Visible in this sectional view is the feed-through pin 130, including the distal end of the feed-through pin 130 attached to the ring anode electrode 120. Also visible in this section view is an electronic assembly 133 on which various electronic components are mounted, including a disc-shaped battery 132. FIG. 3A further illustrates how the cover plate 122 is welded, or otherwise bonded, to the bottom case 124 in order to form the hermetically-sealed IEAD housing 100.

Figure 4:
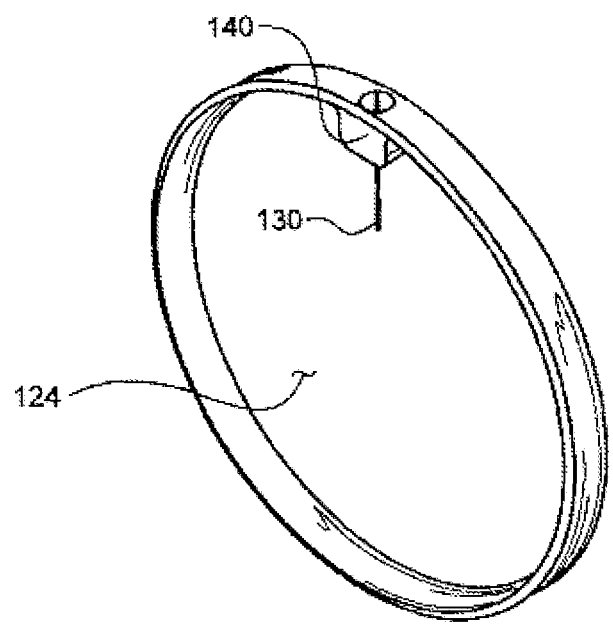
FIG. 4 is a perspective view of the IEAD housing, including a feed-through pin, before the electronic components are placed therein, and before being sealed with a cover plate.

FIG. 4 shows a perspective view of the IEAD case 124, including the feed-through pin 130, before the electronic components are placed therein, and before being sealed with the "skin side" cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 is a key feature of the invention because it keeps the temperature-sensitive portions of the feed-through assembly (those portions that could be damaged by excessive heat) away from the thermal shock and residual weld stress inflicted upon the case 124 when the cover plate 122 is welded thereto.

Figure 4A:
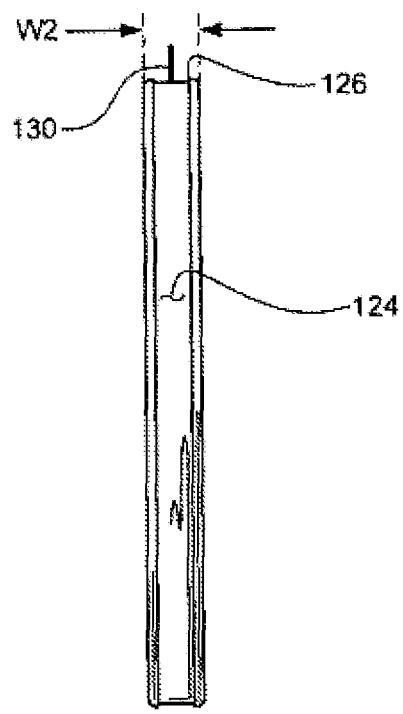
FIG. 4A is a side view of the IEAD housing of FIG. 4.

FIG. 4A is a side view of the IEAD case 124, and shows an annular rim 126 formed on both sides of the case 124. The ring anode electrode 120 fits between these rims 126 once the ring electrode 120 is positioned around the edge of the case 124. (This ring electrode 120 is, for most configurations, used as an anode electrode. Hence, the ring electrode 120 may sometimes be referred to herein as a ring anode electrode. However, it is noted that the ring electrode could also be employed as a cathode electrode, if desired.) A silicone insulator layer 129 (see FIG. 7) is placed between the backside of the ring anode electrode 120 and the perimeter edge of the case 124 where the ring anode electrode 120 is placed around the edge of the case 124.

FIG. 5 shows a plan view of the empty IEAD case 124 shown in the perspective view of FIG. 4. An outline of the recess cavity 140 is also seen in FIG. 5, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 5 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 5A depicts a sectional view of the IEAD housing 124 of FIG. 5 taken along the section line A-A of FIG. 5. FIG. 5B shows an enlarged view or detail of the portion of FIG. 5A that is encircled with the line B. Referring to FIGS. 5A and 5B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 5A and 5B, the diameter D3 is 0.95–0.07 mm, where the −0.07 mm is a tolerance. (Thus, with the tolerance considered, the diameter D3 may range from 0.88 mm to 0.95 mm) The diameter D4 is 0.80 mm with a tolerance of −0.06 mm. (Thus, with the tolerance considered, the diameter D4 could range from 0.74 mm to 0.80 mm).

The feed-through pin 130 is preferably made of pure platinum 99.95%. A preferred material for the insulator material 136 is Ruby or alumina. The IEAD case 124, and the cover 122, are preferably made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed $1 \times 10^{-9}$ STD cc/sec at 1 atm pressure. Other tests are performed to verify the case-to-pin resistance (which should be at least $15 \times 10^6$ Ohms at 100 volts DC), the avoidance of dielectric breakdown or flashover between the pin and the case 124 at 400 volts AC RMS at 60 Hz and thermal shock.

One important advantage provided by the feed-through assembly shown in FIGS. 4A, 5, 5A and 5B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Turning next to FIG. 6, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty bottom housing 124 of FIG. 4 and FIG. 5.

FIGS. 6A and 6B show a plan view and side view, respectively, of the electronic assembly 133 shown in FIG. 6. The electronic components are assembled and connected together so as to perform the circuit functions needed for the IEAD 100 to perform its intended functions. These circuit functions are explained in more detail below under the sub-heading "Electrical Design". Additional details associated with these functions may also be found in many of the patent applications referenced above.

FIG. 7 shows an exploded view of the complete IEAD 100, illustrating its main constituent parts. As seen in FIG. 7, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby insulator 136), the electronic assembly 133 (which includes the battery 132 and various electronic components 134 mounted on a pc board 138) and the cover plate 122. The cover plate 122 is welded to the edge of the bottom case 124 using laser beam welding, or some equivalent process, as one of the final steps in the assembly process.

Other components included in the IEAD assembly, but not necessarily shown or identified in FIG. 7, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 7 is the manner of connecting the proximal end of the feed-through pin 130 to the pc board 138, and connecting a pc board ground pad to the case 124. A preferred method of making these connections is to use conductive epoxy and conductive ribbons, although other connection methods known in the art may also be used.

Further shown in FIG. 7 is a layer of silicon molding 125 that is used to cover all surfaces of the entire IEAD 100 except for the anode ring electrode 120 and the circular cathode electrode 110. An overmolding process is used to accomplish this, although overmolding using silicone LSR 70 (curing temperature of 120° C.) with an injection molding process cannot be used. Overmolding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the preferred configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the one preferred embodiment described above in connection with FIGS. 1, and 2-7. For example, the ring anode electrode 120 need not be placed around the perimeter of the device, but such electrode may be a flat circumferential electrode that assumes different shapes (e.g., round or oval) that is placed on the front or back surface of the IEAD so as to surround the central electrode. Further, for some embodiments, the surfaces of the anode and cathode electrodes may have convex surfaces.

It is also noted that while one preferred embodiment has been disclosed herein that incorporates a round, or short cylindrical-shaped housing, also referred to as a coin-shaped housing, the invention does not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Some particularly attractive alternate case shapes, and electrode placement on the surfaces of those case shapes, are illustrated in Appendix E. Any of these alternate shapes, or others, would still permit the basic principles of the invention to be used to provide a robust, compact, thin, case to house the electronic circuitry and power source used by the invention; as well as to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be readily implanted in a pocket over the tissue area where the selected acupoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the invention apply.

Further, it should be noted that while the preferred configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Finally, it is noted that the electrode arrangement may be modified somewhat, and the desired attributes of the invention may still be achieved. For example, as indicated previously, one preferred electrode configuration for use with the invention utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the invention may still be achieved. For example, two spaced-apart electrodes on a front surface of the housing, one of a first polarity, and a second of a second polarity, could still, when oriented properly with respect to a selected acupoint tissue location, provide some desired therapeutic results.

FIG. 7A schematically illustrates a few alternative electrode configurations that may be used with the invention. The electrode configuration schematically shown in the upper left corner of FIG. 7A, identified as "I", schematically illustrates one central electrode 110 surrounded by a single ring electrode 120. This is one of the preferred electrode configurations that has been described previously in connection, e.g., with the description of FIG. 1 and FIG. 7, and is presented in FIG. 7A for reference and comparative purposes.

In the lower left corner of FIG. 7A, identified as "II", an electrode/array configuration is schematically illustrated that has a central electrode 310 of a first polarity surrounded by an electrode array 320a of two electrodes of a second polarity. When the two electrodes (of the same polarity) in the electrode array 320a are properly aligned with the body tissue being stimulated, e.g., aligned with a nerve 87 (see FIGS. 17A and 17B), then such electrode configuration can stimulate the body tissue (e.g., the nerve 87) at or near the desired acupoint(s) with the same, or almost the same, efficacy as can the electrode configuration I (upper right corner of FIG. 7A).

Note, as has already been described above, the phrase "electrode or electrode array," or "electrodes or electrode arrays," may also be referred to herein as "electrode/array" or "electrodes/arrays," respectively. For the ease of explanation, when an electrode array is referred to herein that comprises a plurality (two or more) of individual electrodes of the same polarity, the individual electrodes of the same polarity within the electrode array may also be referred to as "individual electrodes", "segments" of the electrode array, "electrode segments", or just "segments".

In the lower right corner of FIG. 7A, identified as "III", en electrode configuration is schematically illustrated that has a central electrode/array 310b of three electrode segments of a first polarity surrounded by an electrode array 320b of three electrode segments of a second polarity. As shown in FIG. 7A-III, the three electrode segments of the electrode array 320b are symmetrically positioned within the array 320b, meaning that they are positioned more or less equidistant from each other. However, a symmetrical positioning of the electrode segments within the array is not necessary to stimulate the body tissue at the desired acupoint(s) with some efficacy.

In the upper right corner of FIG. 7A, identified as "IV", an electrode/array configuration is schematically illustrated that has a central electrode array 310c of a first polarity surrounded by an electrode array 320c of four electrode segments of a second polarity. The four electrode segments of the electrode array 320c are arranged symmetrically in a round or oval-shaped array. The four electrode segments of the electrode array 310b are likewise arranged symmetrically in a round or oval-shaped array. While preferred for many configurations, the use of a symmetrical electrode/array, whether as a central electrode array 310 or as a surrounding electrode/array 320, is not always required.

The electrode configurations I, II, III and IV shown schematically in FIG. 7A are only representative of a few electrode configurations that may be used with the present invention. Further, it is to be noted that the central electrode/array 310 need not have the same number of electrode segments as does the surrounding electrode/array 320. Typically, the central electrode/array 310 of a first polarity will be a single electrode; whereas the surrounding electrode/array 320 of a second polarity may have n individual electrode segments, where n is an integer that can vary from 1, 2, 3, . . . n. Thus, for a circumferential electrode array where n=4, there are four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode/array. When n=1, the circumferential electrode array reduces to a single circumferential segment or a single annular electrode that surrounds a central electrode/array.

Additionally, the polarities of the electrode/arrays may be selected as needed. That is, while the central electrode/array 310 is typically a cathode (−), and the surrounding electrode/array 320 is typically an anode (+), these polarities may be reversed.

It should further be noted that the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

Additional electrode configurations, both symmetrical electrode configurations and non-symmetrical electrode configurations, that may be used with an EA stimulation device as described herein, are described and illustrated in Appendix A and Appendix B.

Electrical Design

Next, with reference to FIGS. 8A-14, the electrical design and operation of the circuits employed within the IEAD 100 will be described. More details associated with the design of the electrical circuits described herein may be found in many of the patent applications referenced above.

Figure 8A:
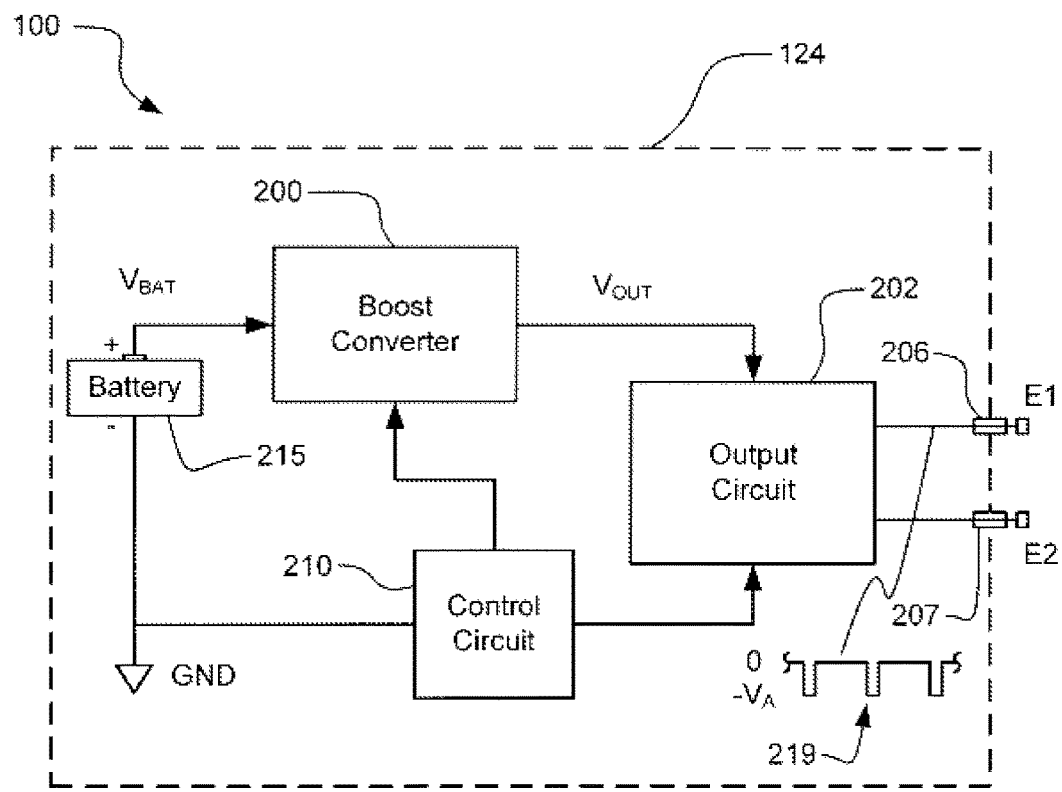
FIG. 8A illustrates a functional block diagram of the electronic circuits used within an IEAD of the type described herein.

FIG. 8A shows a functional block diagram of an implantable electroacupuncture device (IEAD) 100 made in accordance with the teachings disclosed herein. As seen in FIG. 8A, the IEAD 100 uses an implantable battery 215 having a battery voltage $V_{BAT}$. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor $C_C$ is also employed in series with at least one of the feed-through terminals 206 or 207 to prevent DC (direct current) current from flowing into the patient's body tissue.

Figure 15A:
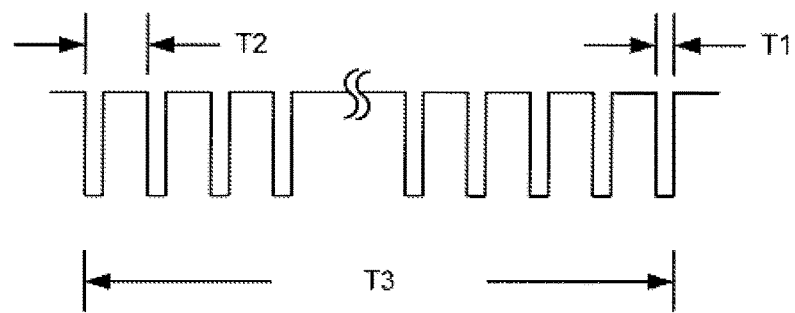
FIG. 15A shows a timing waveform diagram of representative EA stimulation pulses generated by the IEAD device during a stimulation session.

As explained more fully below in connection with the description of FIGS. 15A and 15B, the prescribed stimulation regimen comprises a continuous stream of stimulation pulses having a fixed amplitude (which could be either a fixed voltage or a fixed current), a fixed pulse width, e.g., 0.5 millisecond, and at a fixed frequency, e.g., 2 Hz, during each stimulation session. The stimulation session, also as part of the stimulation regimen, is generated at a very low duty cycle, e.g., for 30 minutes once each week. Other stimulation regimens may also be used, e.g., using a variable frequency for the stimulus pulse during a stimulation session rather than a fixed frequency.

In one preferred embodiment, the electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second preferred embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 8A.

Thus, in the embodiment described in FIG. 8A, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The IEAD 100 shown in FIG. 8A, and packaged as described above in connection with FIGS. 1-7, advantageously provides a tiny self-contained, coin-sized stimulator that may be implanted in a patient at or near a specified acupoint in order to favorably treat a condition or disease of a patient. The coin-sized stimulator advantageously applies electrical stimulation pulses at very low levels and low duty cycles in accordance with specified stimulation regimens through electrodes that form an integral part of the housing of the stimulator. A tiny battery inside of the coin-sized stimulator provides enough energy for the stimulator to carry out its specified stimulation regimen over a period of several years. Thus, the coin-sized stimulator, once implanted, provides an unobtrusive, needleless, long-lasting, safe, elegant and effective mechanism for treating certain conditions and diseases that have long been treated by acupuncture or electroacupuncture.

Figure 8B:
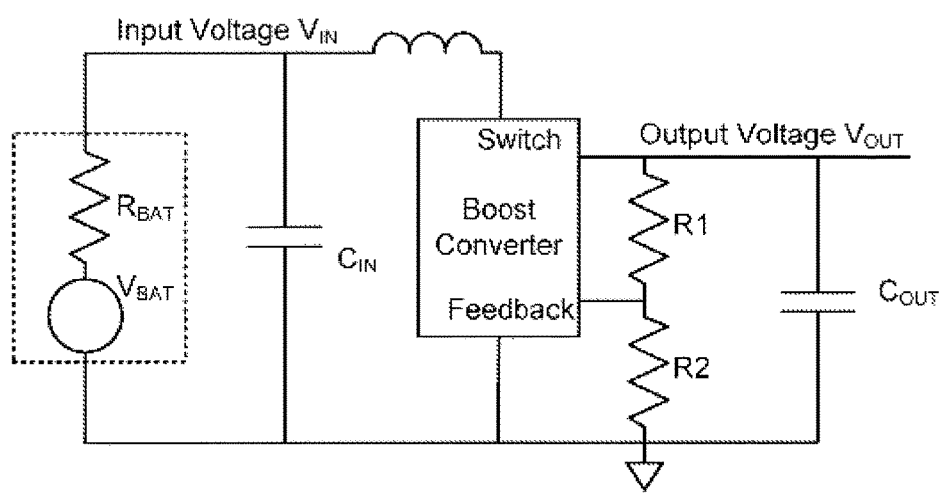
FIG. 8B shows a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 8B. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electroacupuncture device.

In the boost converter circuit example shown in FIG. 8B, the battery is modeled as a voltage source with a simple series resistance. With reference to the circuit shown in FIG. 8B, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 9A, where the horizontal axis is time, and the vertical axis on the left is voltage, and the vertical axis of the right is current.

Figure 9A:
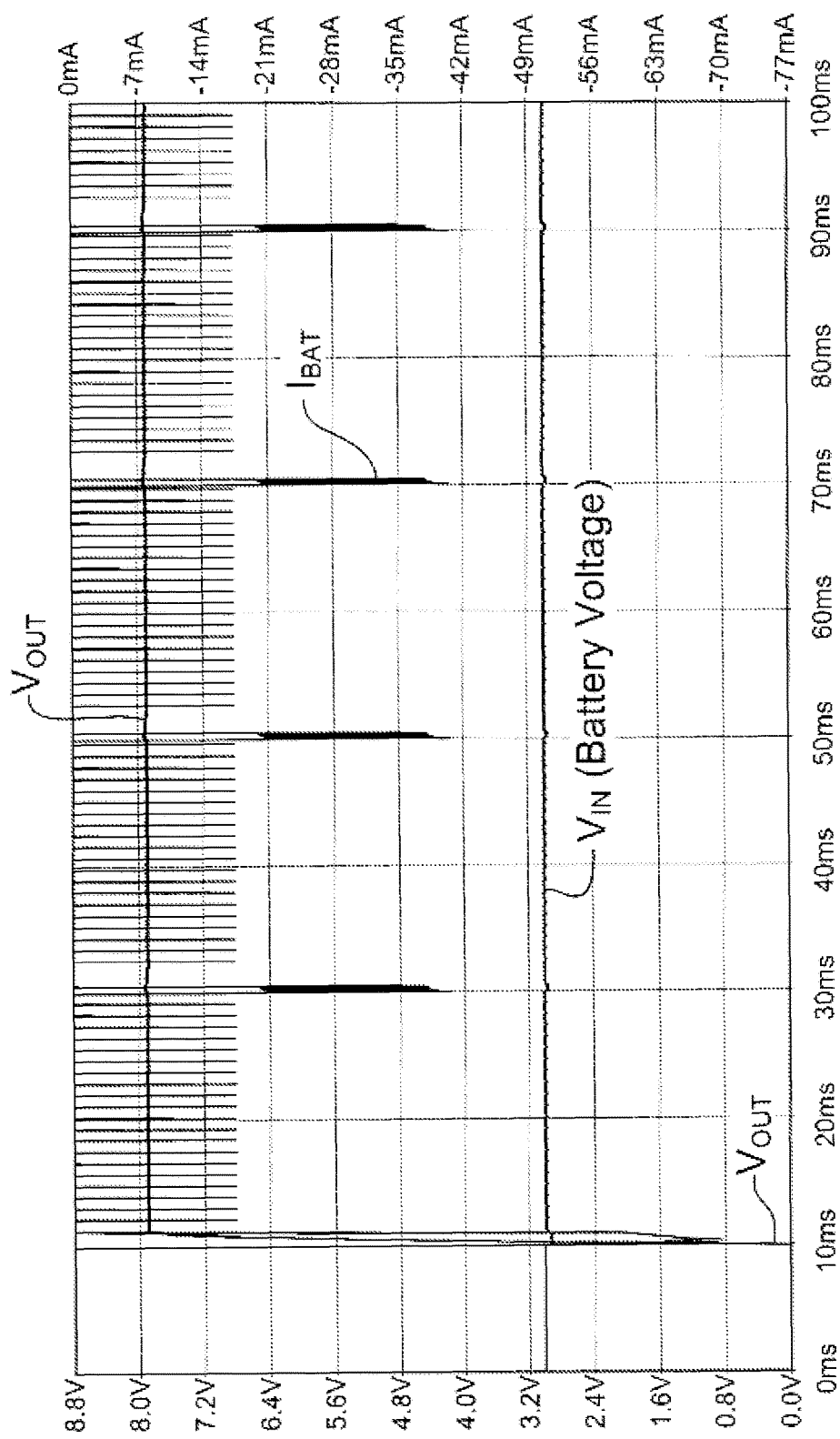
FIG. 9A illustrates a typical voltage and current waveform for the circuit of FIG. 8 when the battery impedance $R_{BAT}$ is small.

Referring to the waveform in FIG. 9A, at boost converter startup (10 ms), there is 70 mA of current drawn from the battery with only ~70 mV of drop in the input voltage $V_{IN}$ (battery voltage). Similarly, the instantaneous output current demand for electro-acupuncture pulses draws up to 40 mA from the battery with an input voltage drop of ~40 mV.

Figure 9B:
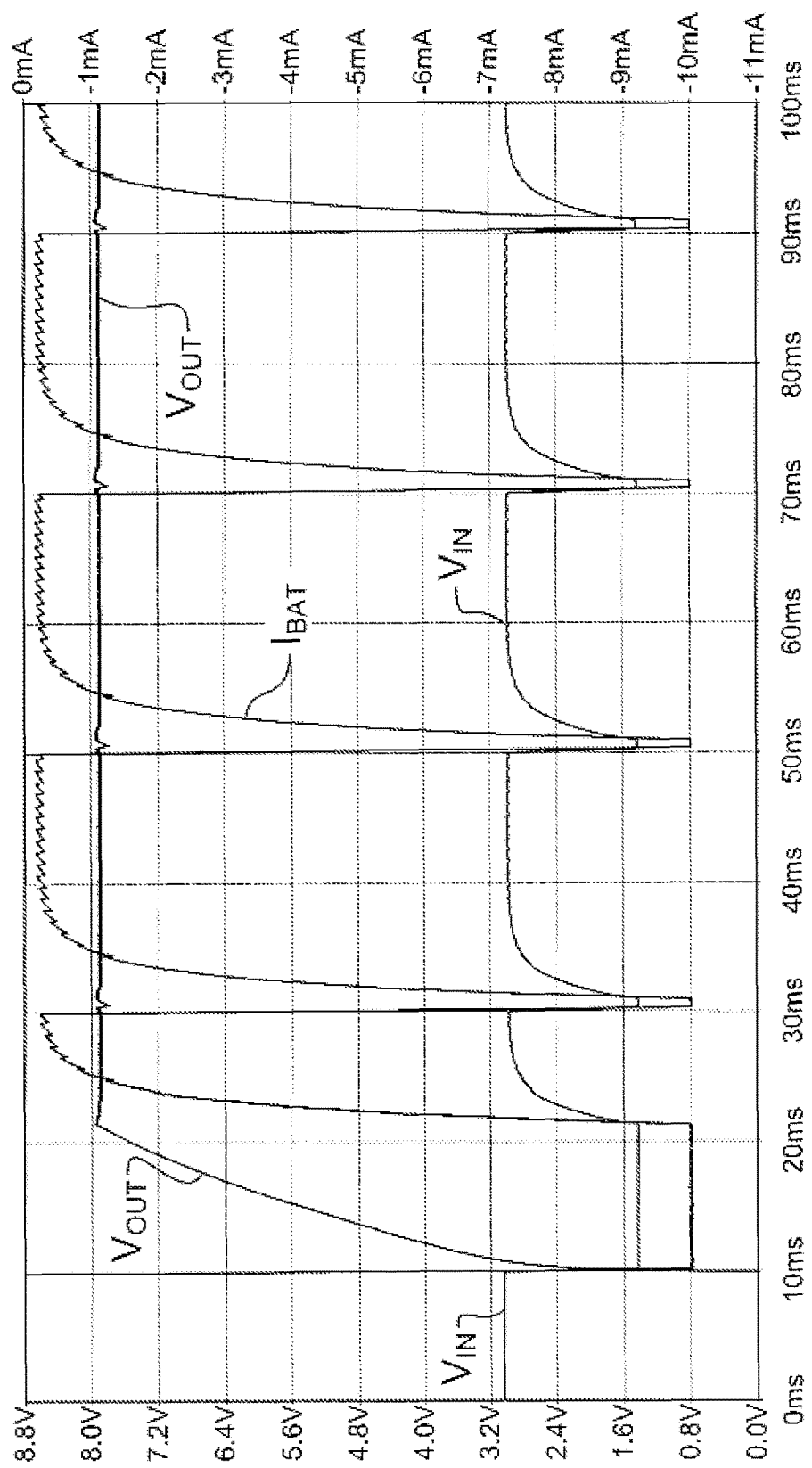
FIG. 9B shows the voltage and current waveform for the circuit of FIG. 8B when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 9B. In FIG. 9B, as in FIG. 9A, the horizontal axis is time, the left vertical axis is voltage, and the right vertical axis is current.

As seen in FIG. 9B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electroacupuncture stimulus pulses. The resulting drops in output voltage $V_{OUT}$ are just not acceptable in any type of circuit except an uncontrolled oscillator circuit.

Also, it should be noted that although the battery used in the boost converter circuit is modeled in FIG. 8B as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing $V_{IN}$ (the battery voltage) to drop to unacceptably low levels as the boost converter circuit pumps up the output voltage $V_{OUT}$ and when there is high instantaneous output current demand, as occurs when EA stimulation pulses are generated.

Figure 10:
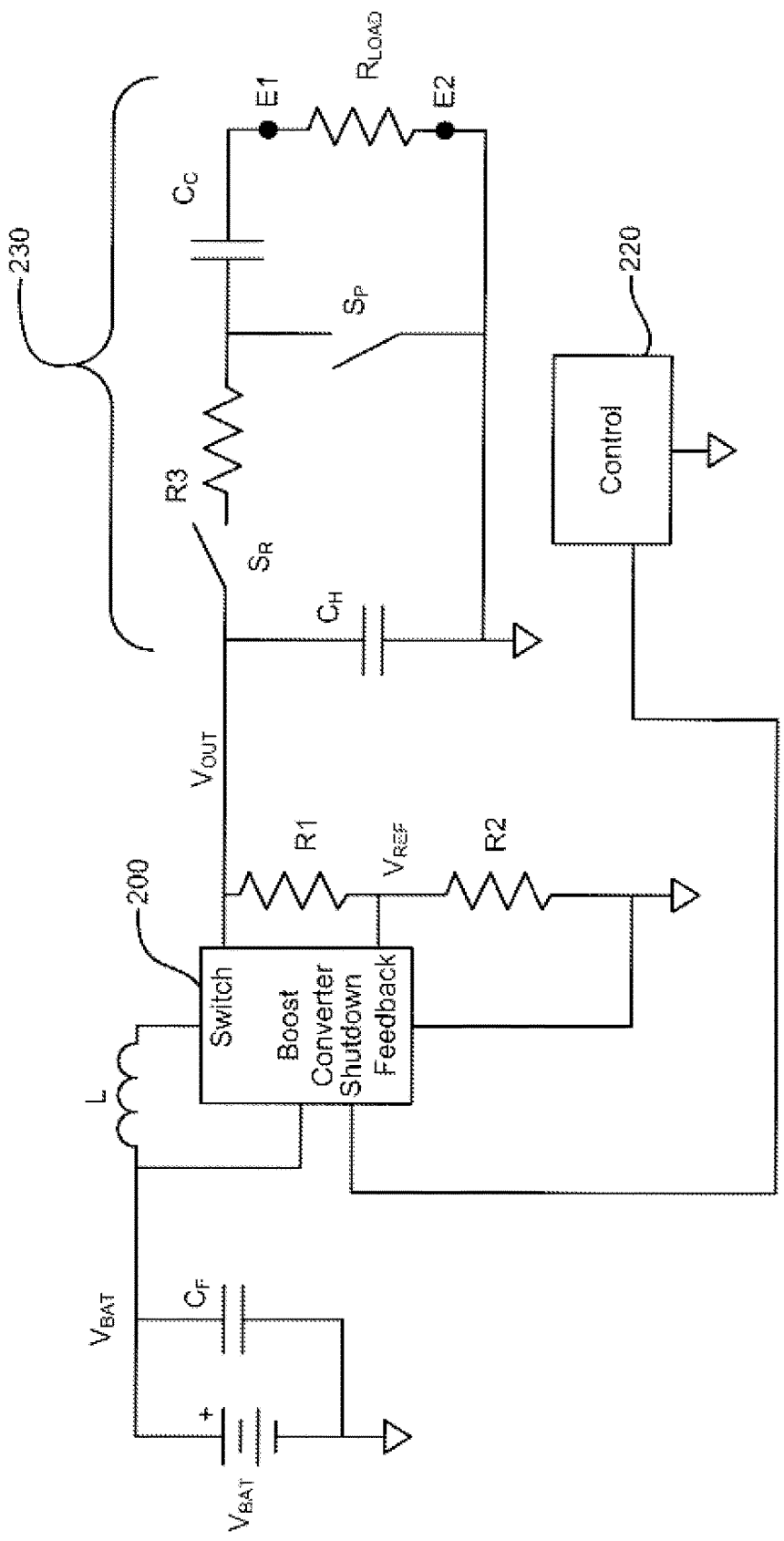
FIG. 10 shows one preferred boost converter circuit and a functional pulse generation circuit configuration for use within the IEAD.

To provide this needed current management, the IEAD 100 disclosed herein employs electronic circuitry as shown in FIG. 10, or equivalents thereof. Similar to what is shown in FIG. 8B, the circuitry of FIG. 10 includes a battery, a boost converter circuit 200, an output circuit 230, and a control circuit 220. The control circuit 220 generates a digital control signal that is used to duty cycle the boost converter circuit 200 ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance $C_F$ is used to reduce the ripple in the battery voltage $V_{BAT}$ (which battery voltage is also the input voltage to the boost converter circuit 200, and is thus also referred to herein as the input voltage $V_{IN}$). The capacitor $C_F$ supplies the high instantaneous current for the short time that the boost converter is ON and then recharges more slowly from the battery during the interval that the boost converter is OFF.

A variation of the above-described use of a digital control signal to duty cycle the boost converter circuit 200 ON and OFF is to let the digital control be generated within the boost converter 200 itself (without having to use a separate control circuit 220). In accordance with this variation, the boost converter circuit 200 shuts itself down whenever the battery voltage falls below a predetermined level above that required by the remaining circuitry. For example, the MAX8570 boost converter IC, commercially available from Maxim, shuts down when the applied voltage falls below 2.5 V. This is still a high enough voltage to ensure the microprocessor and other circuitry remain operational. Thus, as soon as the input voltage drops below 2.5 volts, the boost converter circuit shuts down, thereby limiting the instantaneous current drawn from the battery. When the boost converter shuts down, the instantaneous battery current drawn from the battery is immediately reduced a significant amount, thereby causing the input voltage to increase. The boost converter remains shut down until the microprocessor (e.g., the circuit U2 shown in FIG. 13A, described below), and/or other circuitry used with the boost converter, determine that it is time to turn the boost converter back ON. Once turned ON, the boost converter remains ON until, again, the input voltage drops to below 2.5 volts. This pattern continues, with the boost converter being ON for a short time, and OFF for a much longer time, thereby controlling and limiting the amount of current that can be drawn from the battery.

In the circuitry shown in FIG. 10, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 10, $V_{REF}$ is proportional to the output voltage $V_{OUT}$, as determined by the resistor dividing network of R1 and R2.

The switches $S_P$ and $S_R$, shown in FIG. 10 as part of the output circuit 230, may also be controlled by the control circuit 220. These switches are selectively closed and opened to form the EA stimulation pulses applied to the load, $R_{LOAD}$. Before a stimulus pulse occurs, switch $S_R$ is closed sufficiently long for the circuit side of coupling capacitor $C_C$ to be charged to the output voltage, $V_{OUT}$. The tissue side of $C_C$ is maintained at 0 volts by the cathode electrode E2, which is maintained at ground reference. Then, for most of the time between stimulation pulses, both switches $S_R$ and $S_P$ are kept open, with a voltage approximately equal to the output voltage $V_{OUT}$ appearing across the coupling capacitor $C_C$.

At the leading edge of a stimulus pulse, the switch $S_P$ is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_P$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT3}$, then switch $S_R$ is opened, and both switches $S_R$ and $S_P$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 10, a boost converter circuit 200 is employed which can be shut down with a control signal. The control signal is ideally a digital control signal generated by a control circuit 220 (which may be realized using a microprocessor or equivalent circuit). The control signal is applied to the low side (ground side) of the boost converter circuit 200 (identified as the "shutdown" terminal in FIG. 10). A capacitor $C_F$ supplies instantaneous current for the short ON time that the control signal enables the boost converter circuit to operate. And, the capacitor CF is recharged from the battery during the relatively long OFF time when the control signal disables the boost converter circuit.

Figure 11:
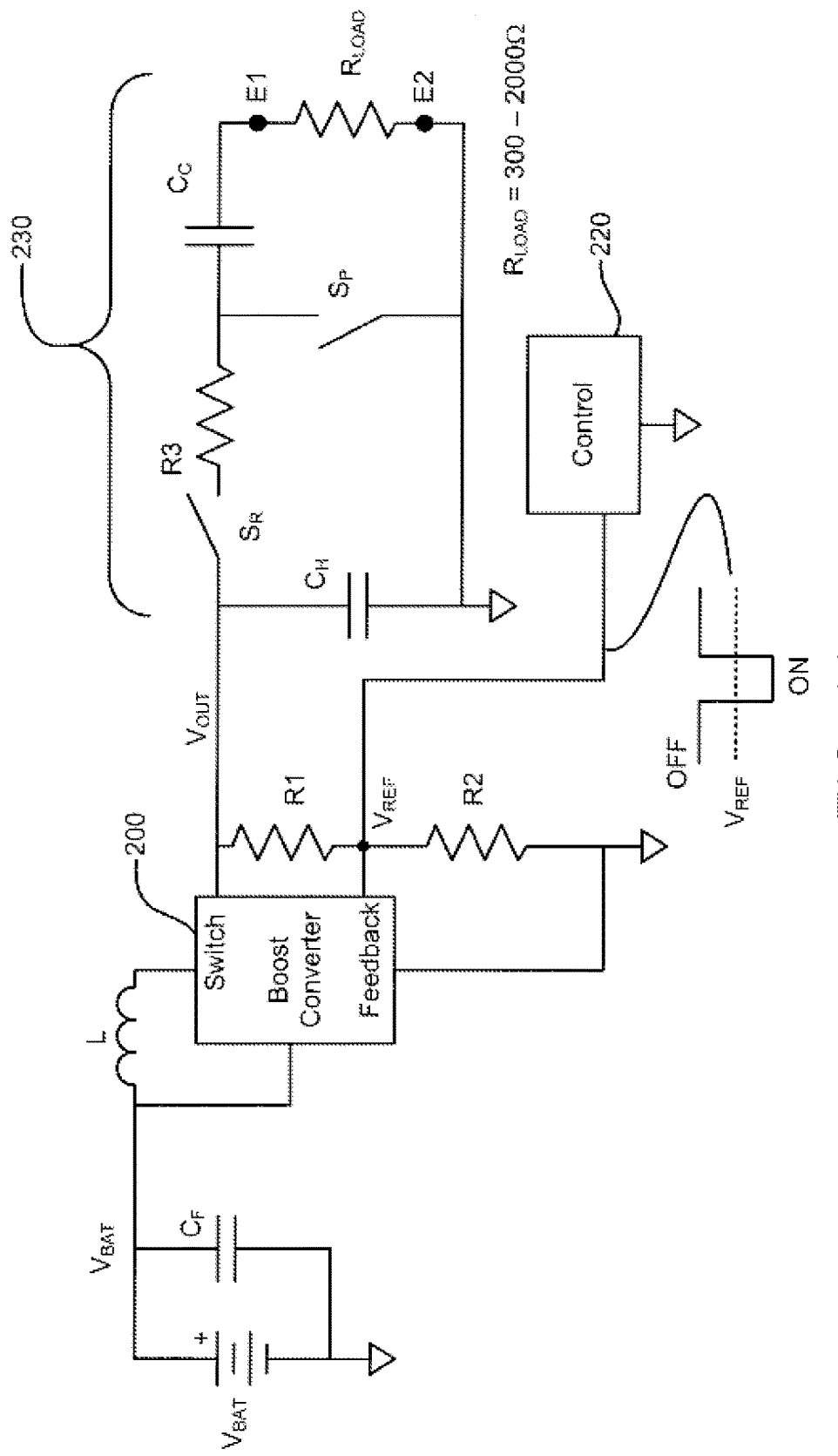
FIG. 11 shows an alternate boost converter circuit configuration and a functional pulse generation circuit for use within the IEAD.

An alternate embodiment of the electronic circuitry that may be used within the IEAD 100 is shown in FIG. 11. This circuit is in most respects the same as the circuitry shown in FIG. 10. However, in this alternate embodiment shown in FIG. 11, the boost converter circuit 200 does not have a specific shut down input control. Rather, as seen in FIG. 11, the boost converter circuit is shut down by applying a control voltage to the feedback input of the boost converter circuit 200 that is higher than $V_{REF}$. When this happens, i.e., when the control voltage applied to the feedback input is greater than $V_{REF}$, the boost converter will stop switching and draws little or no current from the battery. The value of $V_{REF}$ is typically a low enough voltage, such as a 1.2 V band-gap voltage, that a low level digital control signal can be used to disable the boost converter circuit. To enable the boost converter circuit, the control signal can be set to go to a high impedance, which effectively returns the node at the $V_{REF}$ terminal to the voltage set by the resistor divider network formed from R1 and R2. Alternatively the control signal can be set to go to a voltage less than $V_{REF}$.

A low level digital control signal that performs this function of enabling (turning ON) or disabling (turning OFF) the boost converter circuit is depicted in FIG. 11 as being generated at the output of a control circuit 220. The signal line on which this control signal is present connects the output of the control circuit 220 with the $V_{REF}$ node connected to the feedback input of the boost converter circuit. This control signal, as suggested by the waveform shown in FIG. 11, varies from a voltage greater than $V_{REF}$, thereby disabling or turning OFF the boost converter circuit, to a voltage less than $V_{REF}$, thereby enabling or turning the boost converter circuit ON.

Figure 12:
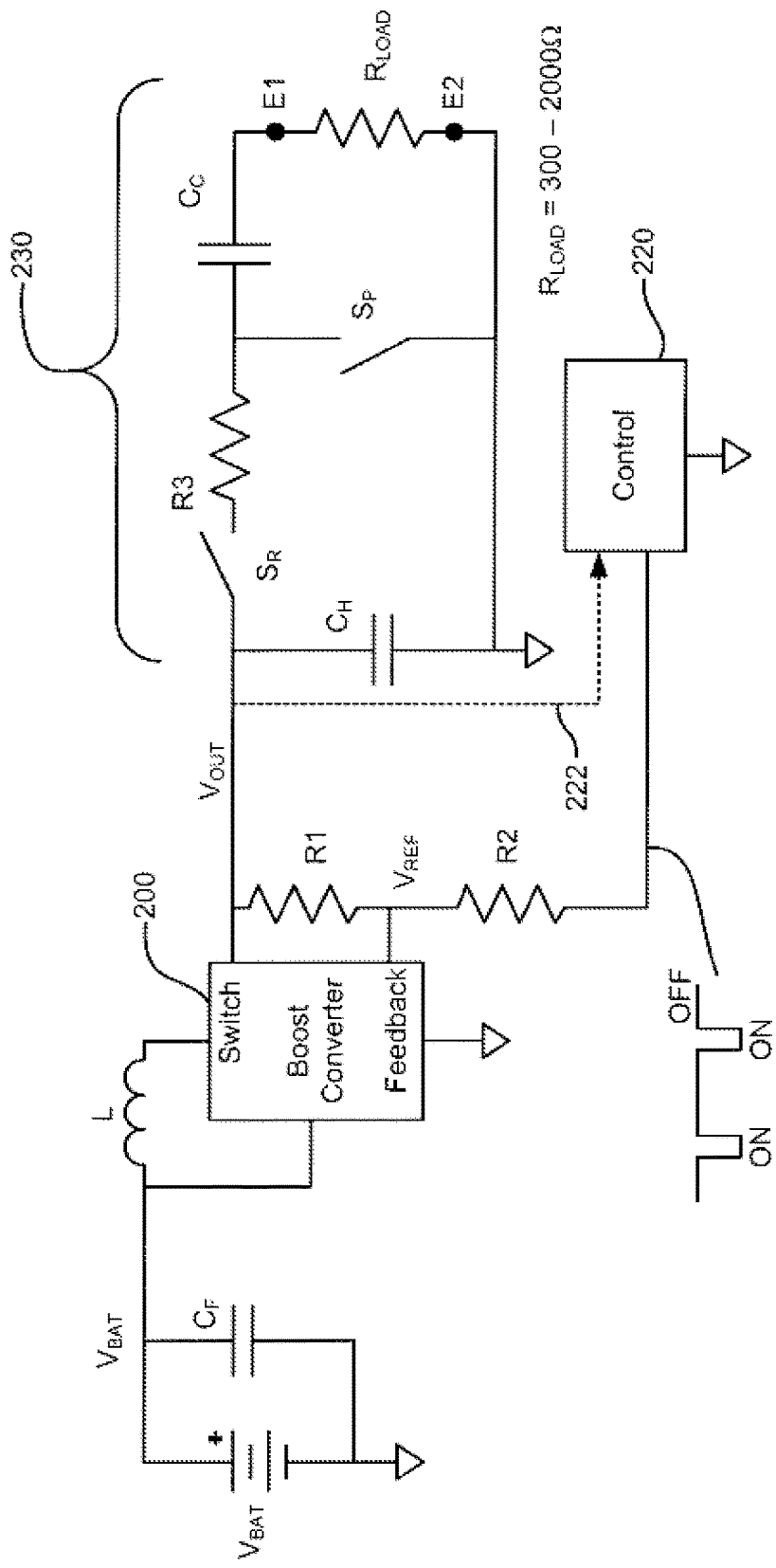
FIG. 12 shows a refinement of the circuit configuration of FIG. 11.

A refinement to the alternate embodiment shown in FIG. 11 is to use the control signal to drive the low side of R2 as shown in FIG. 12. That is, as shown in FIG. 12, the boost converter circuit 200 is shut down when the control signal is greater than $V_{REF}$ and runs when the control signal is less than $V_{REF}$. A digital control signal can be used to perform this function by switching between ground and a voltage greater than $V_{REF}$. This has the additional possibility of delta-sigma modulation control of $V_{OUT}$ if a measurement of the actual $V_{OUT}$ is available for feedback, e.g., using a signal line 222, to the controller.

Figure 13A:
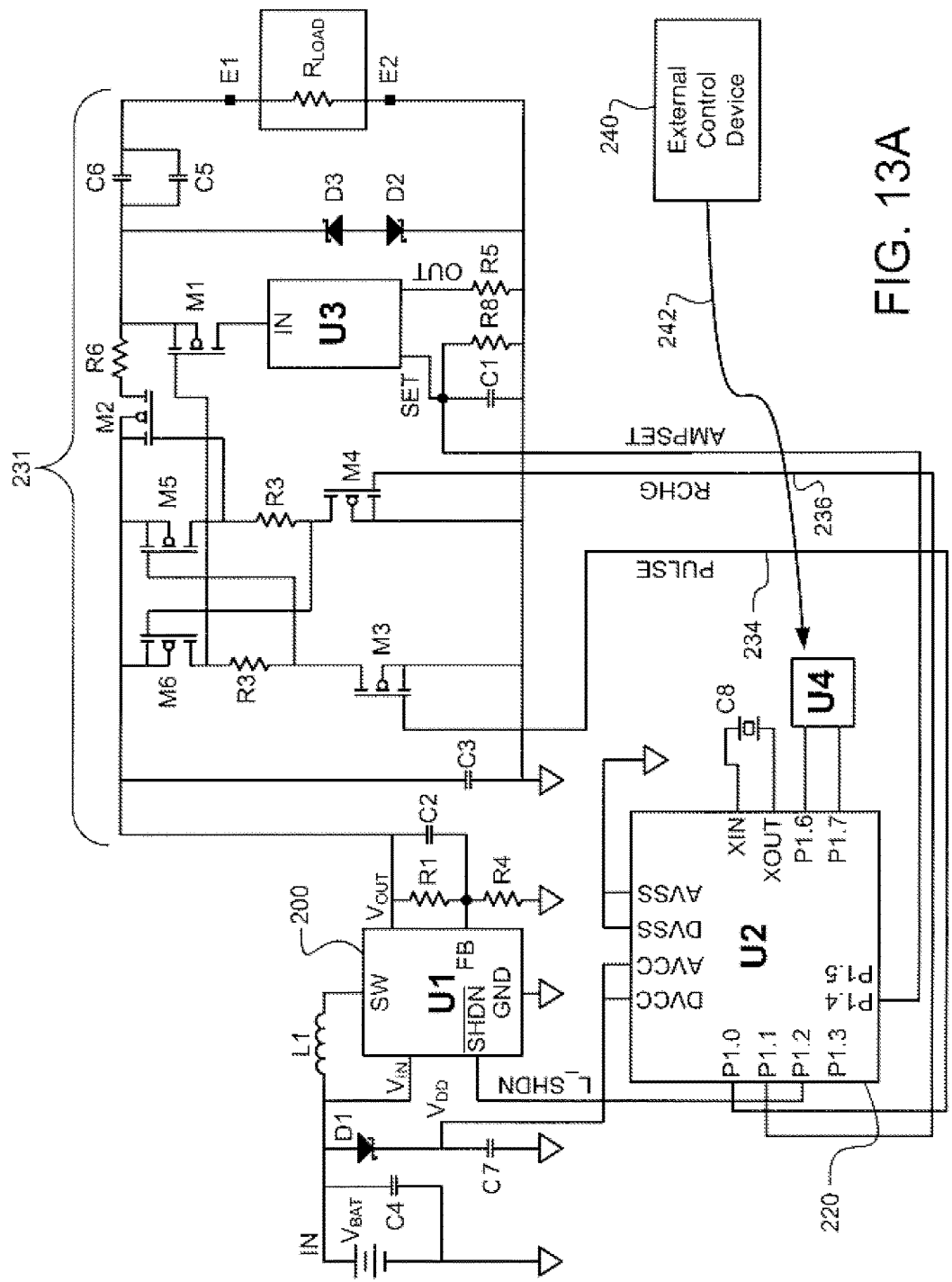
FIG. 13A shows one preferred schematic configuration for an implantable electroacupuncture device (IEAD) that utilizes the boost converter configuration shown in FIG. 10.

One preferred embodiment of the circuitry used in an implantable electroacupuncture device (IEAD) 100 that employs a digital control signal as taught herein is shown in the schematic diagram shown in FIG. 13A. In FIG. 13A, there are basically four integrated circuits (ICs) used as the main components. The IC U1 is a boost converter circuit, and performs the function of the boost converter circuit 200 described previously in connection with FIGS. 8B, 10, 11 and 12.

The IC U2 is a micro-controller IC and is used to perform the function of the control circuit 220 described previously in connection with FIGS. 10, 11 and 12. A preferred IC for this purpose is a MSP430G2452I micro-controller chip made by Texas Instruments. This chip includes 8 KB of Flash memory. Having some memory included with the micro-controller is important because it allows the parameters associated with a selected stimulation regimen to be defined and stored. One of the advantages of the IEAD described herein is that it provides a stimulation regimen that can be defined with just 5 parameters, as taught below in connection with FIGS. 15A and 15B. This allows the programming features of the micro-controller to be carried out in a simple and straightforward manner.

The micro-controller U2 primarily performs the function of generating the digital signal that shuts down the boost converter to prevent too much instantaneous current from being drawn from the battery $V_{BAT}$, for those embodiments of the invention where this function is needed. The micro-controller U2 also controls the generation of the stimulus pulses at the desired pulse width and frequency. It further keeps track of the time periods associated with a stimulation session, i.e., when a stimulation session begins and when it ends.

The micro-controller U2 also controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current pulled through the closed switch M1, which is essentially the same current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drops across the switches and current source.

The switches $S_R$ and $S_P$ described previously in connection with FIGS. 10, 11 and 12 are realized with transistor switches M1, M2, M3, M4, M5 and M6, each of which is controlled directly or indirectly by control signals generated by the micro-controller circuit U2. For the embodiment shown in FIG. 13A, these switches are controlled by two signals, one appearing on signal line 234, labeled PULSE, and the other appearing on signal line 236, labeled RCHG (which is an abbreviation for "recharge"). For the circuit configuration shown in FIG. 13A, the RCHG signal on signal line 236 is always the inverse of the PULSE signal appearing on signal line 234. This type of control does not allow both switch M1 and switch M2 to be open or closed at the same time. Rather, switch M1 is closed when switch M2 is open, and switch M2 is closed, when switch M1 is open. When switch M1 is closed, and switch M2 is open, the stimulus pulse appears across the load, $R_{LOAD}$, with the current flowing through the load, $R_{LOAD}$, being essentially equal to the current flowing through resistor R5. When the switch M1 is open, and switch M2 is closed, no stimulus pulse appears across the load, and the coupling capacitors C5 and C6 are recharged through the closed switch M2 and resistor R6 to the voltage $V_{OUT}$ in anticipation of the next stimulus pulse.

The circuitry shown in FIG. 13A is only exemplary of one type of circuit that may be used to control the pulse width, amplitude, frequency, and duty cycle of stimulation pulses applied to the load, $R_{LOAD}$. Any type of circuit, or control, that allows stimulation pulses of a desired magnitude (measured in terms of pulse width, frequency and amplitude, where the amplitude may be measured in current or voltage) to be applied through the electrodes to the patient at the specified acupoint at a desired duty cycle (stimulation session duration and frequency) may be used. However, for the circuitry to perform its intended function over a long period of time, e.g., years, using only a small energy source, e.g., a small coin-sized battery having a high battery impedance and a relatively low capacity, the circuitry must be properly managed and controlled to prevent excessive current draw from the battery.

It is also important that the circuitry used in the IEAD 100, e.g., the circuitry shown in FIGS. 10, 11, 12, 13A, or equivalents thereof, have some means for controlling the stimulation current that flows through the load, $R_{LOAD}$, which load may be characterized as the patient's tissue impedance at and around the acupoint being stimulated. This tissue impedance, as shown in FIGS. 11 and 12, may typically vary from between about 300 ohms to 2000 ohms. Moreover, it not only varies from one patient to another, but it varies over time. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 13A, is one way to satisfy this need.

Still referring to FIG. 13A, a fourth IC U4 is connected to the micro-controller U2. For the embodiment shown in FIG. 13A, the IC U4 is an electromagnetic field sensor, and it allows the presence of an externally-generated (non-implanted) electromagnetic field to be sensed. An "electromagnetic" field, for purposes of this application includes magnetic fields, radio frequency (RF) fields, light fields, and the like. The electromagnetic sensor may take many forms, such as any wireless sensing element, e.g., a pickup coil or RF detector, a photon detector, a magnetic field detector, and the like. When a magnetic sensor is employed as the electromagnetic sensor U4, the magnetic field is generated using an External Control Device (ECD) 240 that communicates wirelessly, e.g., through the presence or absence of a magnetic field, with the magnetic sensor U4. (A magnetic field, or other type of field if a magnetic field is not used, is symbolically illustrated in FIG. 13A by the wavy line 242.) In its simplest form, the ECD 240 may simply be a magnet, and modulation of the magnetic field is achieved simply by placing or removing the magnet next to or away from the IEAD. When other types of sensors (non-magnetic) are employed, the ECD 240 generates the appropriate signal or field to be sensed by the sensor that is used.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth.

Another coding scheme that could be used is a sequence-based coding scheme. That is, application of 3 magnetic pulses may be used to signal one external command, if the sequence is repeated 3 times. A sequence of 2 magnetic pulses, repeated twice, may be used to signal another external command. A sequence of one magnetic pulse, followed by a sequence of two magnetic pulses, followed by a sequence of three magnetic pulses, may be used to signal yet another external command.

Other simple coding schemes may also be used, such as the letters AA, RR, HO, BT, KS using international Morse code. That is, the Morse code symbols for the letter "A" are dot dash, where a dot is a short magnetic pulse, and a dash is a long magnetic pulse. Thus, to send the letter A to the IEAD 100 using an external magnet, the user would hold the magnet over the area where the IEAD 100 is implanted for a short period of time, e.g., one second or less, followed by holding the magnet over the IEAD for a long period of time, e.g., more than one second.

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Figure 13B:
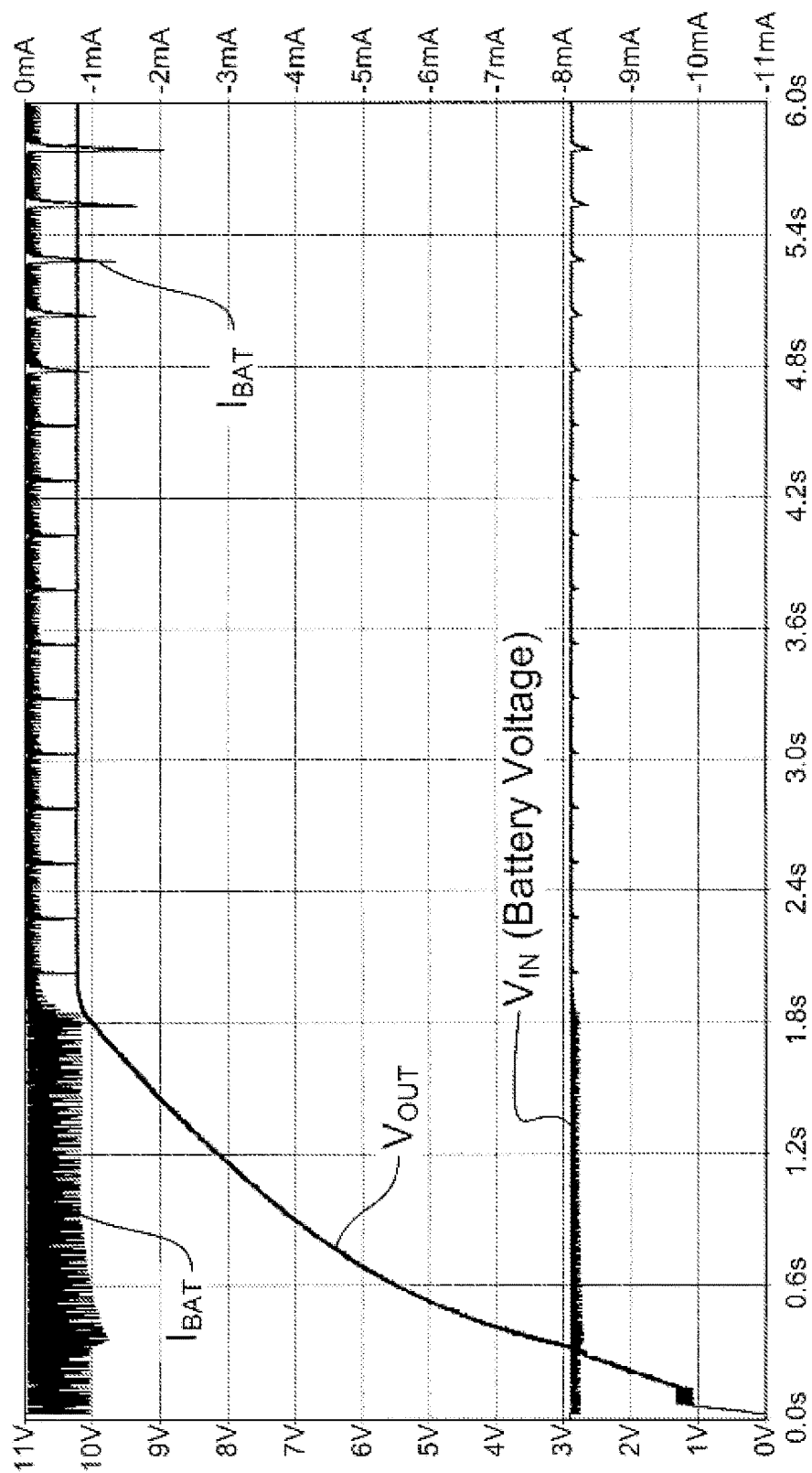
FIG. 13B shows current and voltage waveforms associated with the operation of the circuit shown in FIG. 13A.

The current and voltage waveforms associated with the operation of the IEAD circuitry of FIG. 13A are shown in FIG. 13B. In FIG. 13B, the horizontal axis is time, the left vertical axis is voltage, and the right vertical axis is current. The battery in this example has 160 Ohms of internal impedance.

Referring to FIGS. 13A and 13B, during startup, the boost converter ON time is approximately 30 microseconds applied every 7.8 milliseconds. This is sufficient to ramp the output voltage $V_{OUT}$ up to over 10 V within 2 seconds while drawing no more than about 1 mA from the battery and inducing only 150 mV of input voltage ripple.

The electroacupuncture (EA) simulation pulses resulting from operation of the circuit of FIG. 13A have a width of 0.5 milliseconds and increase in amplitude from approximately 1 mA in the first pulse to approximately 15 mA in the last pulse. The instantaneous current drawn from the battery is less than 2 mA for the EA pulses and the drop in battery voltage is less than approximately 300 mV. The boost converter is enabled (turned ON) only during the instantaneous output current surges associated with the 0.5 milliseconds wide EA pulses.

Figure 14:
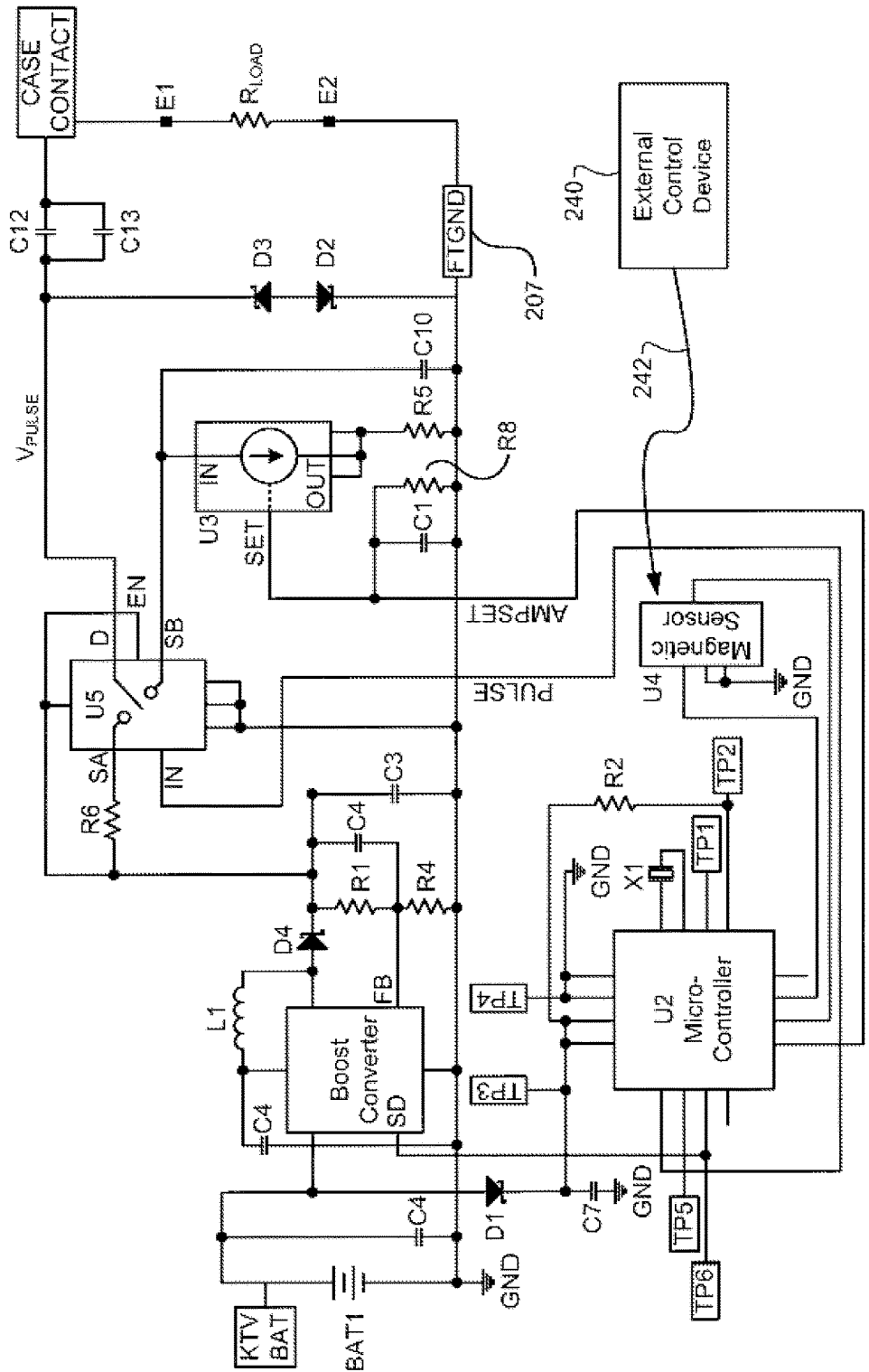
FIG. 14 shows another preferred schematic configuration for an IEAD similar to that shown in FIG. 13A, but which uses an alternate output circuitry configuration for generating the stimulus pulses.

Another preferred embodiment of the circuitry used in an implantable electroacupuncture device (IEAD) 100 that employs a digital control signal as taught herein is shown in the schematic diagram of FIG. 14. The circuit shown in FIG. 14 is, in most respects, very similar to the circuit described previously in connection with FIG. 13A. What is new in FIG. 14 is the inclusion of an external Schottky diode D4 at the output terminal LX of the boost convertor U1 and the inclusion of a fifth integrated circuit (IC) U5 that essentially performs the same function as the switches M1-M6 shown in FIG. 13A.

The Schottky diode D5 helps isolate the output voltage $V_{OUT}$ generated by the boost converter circuit U1. This is important in applications where the boost converter circuit U1 is selected and operated to provide an output voltage $V_{OUT}$ that is four or five times (or more) as great as the battery voltage, $V_{BAT}$. For example, in the embodiment for which the circuit of FIG. 14 is designed, the output voltage $V_{OUT}$ is designed to be nominally 15 volts using a battery that has a nominal battery voltage of only 3 volts. (In contrast, the embodiment shown in FIG. 13A is designed to provide an output voltage that is nominally 10-12 volts, using a battery having a nominal output voltage of 3 volts.)

The inclusion of the fifth IC U5 in the circuit shown in FIG. 14 is, as indicated, used to perform the function of a switch. The other ICs shown in FIG. 14, U1 (boost converter), U2 (micro-controller), U3 (voltage controlled programmable current source) and U4 (electromagnetic sensor) are basically the same as the IC's U1, U2, U3 and U4 described previously in connection with FIG. 13A.

The IC U5 shown in FIG. 14 functions as a single pole/double throw (SPDT) switch. Numerous commercially-available ICs may be used for this function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

From the above description, it is seen that an implantable IEAD 100 is provided that uses a digital control signal to duty-cycle limit the instantaneous current drawn from the battery by a boost converter. Three different exemplary configurations (FIGS. 10, 11 and 12) are taught for achieving this desired result, and two exemplary circuit designs that may be used to realize this result have been disclosed (FIGS. 13A and 14). One configuration (FIG. 12) teaches the additional capability to delta-sigma modulate the boost converter output voltage.

Delta-sigma modulation is well described in the art. Basically, it is a method for encoding analog signals into digital signals or higher-resolution digital signals into lower-resolution digital signals. The conversion is done using error feedback, where the difference between the two signals is measured and used to improve the conversion. The low-resolution signal typically changes more quickly than the high-resolution signal and it can be filtered to recover the high resolution signal with little or no loss of fidelity. Delta-sigma modulation has found increasing use in modern electronic components such as converters, frequency synthesizers, switched-mode power supplies and motor controllers. See, e.g., Wikipedia, Delta-sigma modulation.

Figure 18:
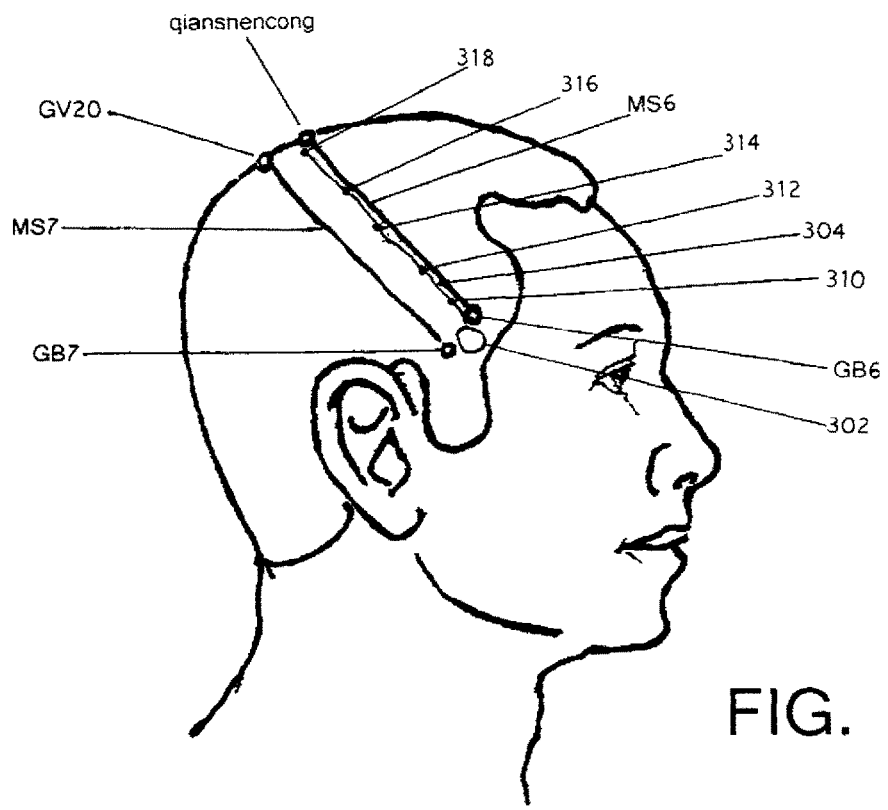
FIG. 18 is a diagram showing the location of the chorea line and an IEAD device on the scalp.

Referring to FIGS. 18-23, an alternative embodiment of the implantable electroacupuncture device (IEAD) 300 is provided. Referring to FIG. 18, a line on the scalp, known as the chorea line and identified on the diagram as MS6, is known to include acupoints which have been used to treat Parkinson's Disease and other conditions which exhibit similar symptoms such as involuntary tremors. Acupuncture and electro acupuncture have been used along the chorea line to treat these conditions. The IEAD 300 depicted in FIGS. 18-23 illustrates a device which is implantable under the skin and provides electrical stimulation at multiple points along the chorea line. The chorea line is a line that begins about a centimeter anterior to acupoint GV20 and follows parallel to the Motor Area Line (identified as MS7 in FIG. 18). The chorea line is located parallel with and about 1.5 cm anterior to the Motor Area Line. As shown in FIG. 18, the housing 302 is implanted under the skin in the area of the chorea line, and the conduit 304 is implanted under the skin in a line which follows the chorea line. The location of the chorea line, or any acupoints found on the chorea line, may vary somewhat among individuals, and may vary somewhat from what is shown in FIG. 18.

The IEADs 300 shown in FIGS. 18-23 include internal circuitry which is similar in layout and function to that which is shown and described for the other embodiments. In other words, the IEADs shown in FIGS. 18-23 include a housing 302 which is similar in form and function to the device 100 illustrated in the other embodiments, meaning that the housing 302 includes circuitry suitable for providing electrical pulses to one or more leads 310 according to a defined schedule, as is described herein. Housing 302 includes a conduit 304 which extends from the housing 302. The conduit 304 carries one or more leads 310, and each lead 310 includes one or more electrodes 312. Two variations of this embodiment are illustrated: in FIGS. 20 and 21 a multiple-lead version is illustrated, and in FIGS. 22 and 23 a single-lead version is illustrated. Each lead 310 facilitates electrical communication between the circuitry in the housing 302 and one or electrodes 312, as will be described in greater detail below. The conduit 304 is a hollow tube having an outer wall 316 which defines an interior cavity 318 which extends the length of the conduit and carries the lead(s) 310. One or more opening 314 is formed in the outer wall 316 and one or more electrode 312 is located proximate to each opening 314 such that the tissue proximate each opening 314 is stimulated by the corresponding electrode 312.

Figure 24:
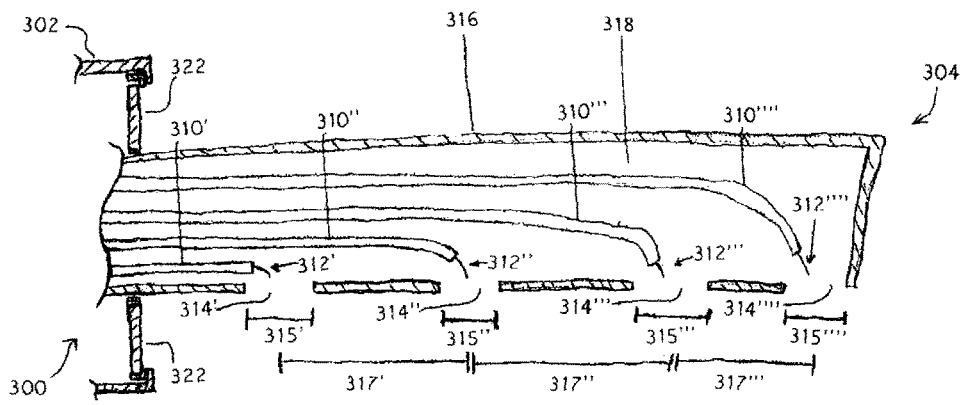
FIG. 24 depicts the IEAD of FIG. 18 having a conduit with multiple openings and carrying a plurality of leads with markings identifying the dimension and spacing of the openings.
Figure 25:
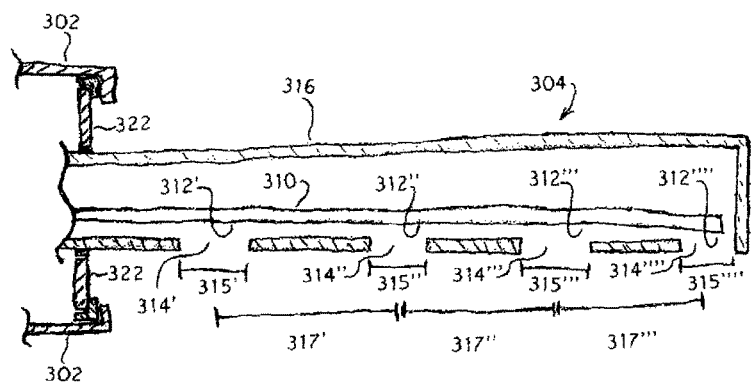
FIG. 25 depicts the IEAD of FIG. 18 having a conduit with multiple openings and carrying a single lead with marking identifying the dimension and spacing of the openings.

Referring to FIGS. 24 and 25, each opening 314 has a dimension 315, as measured along the longitudinal length of the conduit 304. The openings 314 are spaced apart by a distance 317, as measured from the center of a given opening to the center of an opening adjacent the given opening.

In one embodiment, an electrode 322 is carried on the exterior of the housing 302. The electrode 322 is insulated from the housing 302. In another embodiment, the electrode 322 is omitted and some subset of electrodes 312 are cathodes and some subset of electrodes 312 are anodes, as described in greater detail below with reference to FIG. 20.

Figure 19:
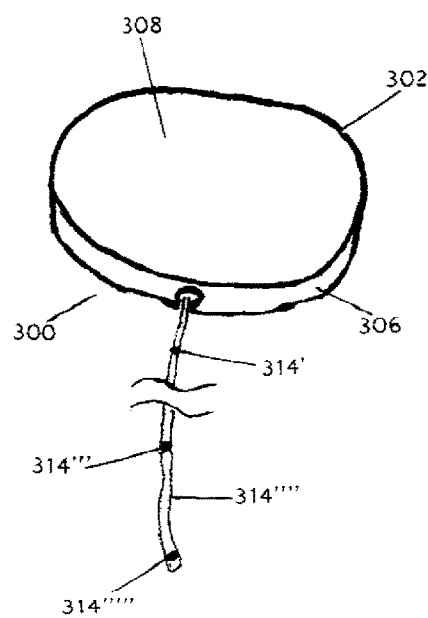
FIG. 19 shows a perspective view of the IEAD of FIG. 18 including a conduit extending therefrom.

Referring to FIG. 19, a perspective view of the IEAD 300 is provided. The housing 302 is a hermetically sealed housing which carries the same, or functionally equivalent, components described above and illustrated in FIGS. 6A and 6B. A conduit 304 extends from the housing 302. Here, the conduit 304 is shown as extending from the perimeter edge 306 of the housing. In other embodiments, the conduit 304 extends from the top face 308 or the bottom face (not shown) of the housing 302. The conduit 304 includes one or more openings 314. The number of openings 314 may vary among embodiments, the preferred embodiment having 2-6 openings. The number of openings in a particular embodiment is selected based on the number and spacing of acupoints on the chorea line of the individual in which the IEAD 300 is to be implanted. An electrode 312 is located proximate each of the openings 314, such that the tissue in the proximity of the respective opening 314 is stimulated according to the parameters configured in the device. For reference purposes, primed numbers will be used to refer to objects which are in proximity with one another, for example, the electrode 312' is located proximate the opening 314' and the electrode 312" is part of lead 310" and so forth.

Figure 20:
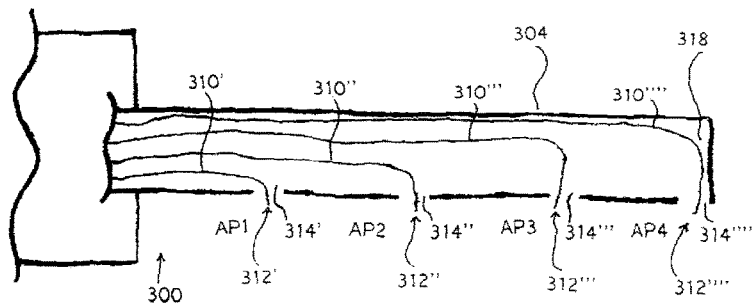
FIG. 20 depicts the IEAD of FIG. 18 having a conduit which carries a plurality of leads.
Figure 21:
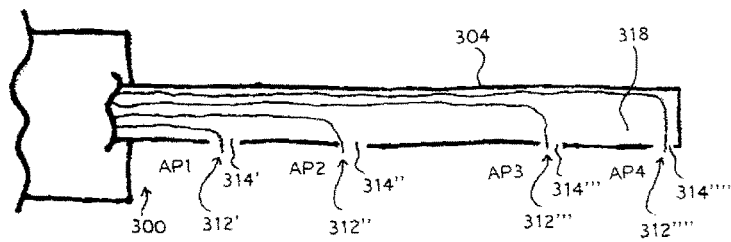
FIG. 21 depicts the IEAD of FIG. 18 having a conduit which carries a plurality of leads, and the conduit has non-uniformed spaced openings.
Figure 22:
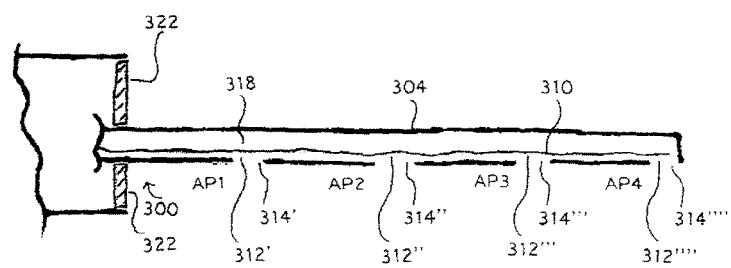
FIG. 22 depicts the IEAD of FIG. 18 having a conduit with multiple openings and which carries a single lead.
Figure 23:
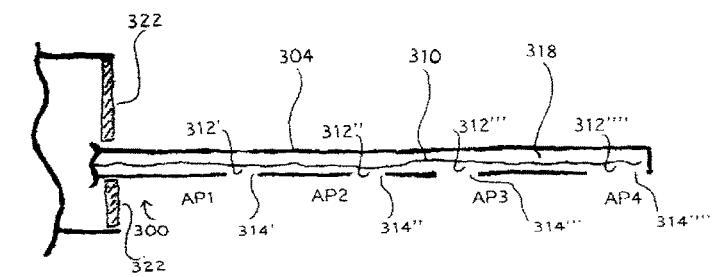
FIG. 23 depicts the IEAD of FIG. 18 having a conduit with multiple openings of varying sizes and which carries a single lead.

FIGS. 20 and 21 illustrate IEADs which include a plurality of leads, one for each opening. FIGS. 22 and 23 illustrate IEADs which each include a single lead, which lead provides stimulation at each opening.

Referring to FIGS. 20 and 21, these Figures show an embodiment where multiple leads 310', 310", 310'" and 310"" are carried within the conduit 304. Each lead 310', 310", 310'" and 310"" is in electrical communication with the circuitry in the housing 302. Each lead 310', 310", 310'" and 310"" terminates in an electrode, 312', 312", 312'" and 312"" respectively. Each electrode 312', 312", 312'" and 312"" is positioned adjacent a respective opening 314', 314", 314'", and 314"" formed through the outer wall 316 of the conduit 204. Referring to FIG. 20, a series of acupoints, identified as AP1, AP2, AP3 and AP4 are spaced along the chorea line and are adjacent the conduit 304. The positions of the various acupoints in this example are not located directly adjacent the openings 314', 314", 314'", and 314"", but are unevenly spaced along the chorea line. The openings 314', 314", 314'", and 314"" are evenly spaced along the length of the conduit 304. When a precise physical location of the electrode(s) is not achieved by placement of the openings, electrical fields emanating from two or more electrodes of the EA device may be combined or superimposed so as to create a virtual electrode whose virtual position may be finely adjusted to be precisely at the desired location along the conduit. As illustrated in FIG. 20, the acupoints AP1, AP2, AP3 and AP4 are not perfectly aligned with the openings 314', 314", 314'", and 314"", and as such, to properly treat AP2, it may be desired to combine the electrical fields emanating from some combination of electrodes 312', 312", 312'", and 312"" to create a virtual electrode which is at or near the location of AP2. For example, if three electrodes 312 were employed, a first of which sources 200 microamps (ma) of current, and thus functions as an anode, and a second and third of which each sink 100 ma, each thus functioning as cathodes, the resulting electric fields would make it appear that a virtual electrode existed at some point along a mid-point line between the second and third electrodes. Such steering of a virtual electrode would thus allow the effectiveness of the EA stimulation to be adjusted or tuned, which effectiveness is largely a function of the proximity between the acupoint site and the electrode. Advantageously, this adjustment, or tuning, can occur even after the IEAD 300 is implanted with a fixed physical location of the electrodes relative to the desired acupoint site. It is appreciated that such steering is possible with any combination of two or more electrodes 312 on the IEAD 300. It is also appreciated that any of the electrodes 312', 312", 312'", or 312"" could be selectively used as either an anode or a cathode according to the programming in the circuitry in the housing 302.

Referring to FIG. 21, the acupoints AP1, AP2, AP3 and AP4 are positioned adjacent the respective openings 314', 314", 314'", and 314"". As shown, the openings 314', 314", 314'", and 314"" are unevenly spaced along the conduit, such that the openings are proximate the acupoints AP1, AP2, AP3 and AP4. The IEAD 300 shown in FIG. 21 would either be custom built with openings 314 and electrodes 312 which are either (a) proximate the acupoints of a given patient, or (b) correspond roughly with the spacing of acupoints on most patients. The uneven spacing provided in FIG. 21 is readily combinable with the virtual electrodes described above for FIG. 20 to further fine-tune the IEAD 300 for a given patient.

Referring to FIGS. 22 and 23, an IEAD 300 is provided having a conduit 304 extending therefrom, which conduit 304 defines a cavity 318 which carries a single lead 310. The conduit 304 includes one or more openings 314 spaced along the length of the conduit 304. The lead 310 is a wire which defines an electrode at each opening 314 in the conduit 304. The lead 310 is in electrical communication with the circuitry in the housing 302. As illustrated in FIG. 22, the openings 314 are evenly spaced along the length of the conduit 304, while the acupoints AP1, AP2, AP3 and AP4 are unevenly spaced relative the openings 314. When the IEAD 300 is activated and electrical fields emanate from the electrodes 312, electrical fields will emanate from each electrode 312 simultaneously, since each of the electrodes 312 are formed as part of the same lead 310. Each of the electrodes 312 on the lead 310 will have the same polarity (either an anode or a cathode), for simplicity of reference, the electrodes are described as being cathodes. An anode 322 will preferably be formed as part of the housing 302, such as formed as a ring circumscribing the perimeter of the housing 302, such as having a geometry described for the anode electrode 120 above. In one instance, the polarity is such that the ring or case of the device is the stimulating anode and the electrodes at the acupoints are cathodes. For this application, it is preferable to have the feed-through wire connected as the cathodes and the case connected as the anode. Additional cathodes would then require additional feed through wires. For the electrode arrays in FIGS. 22 and 23, however, the cathode could be connected either to the feed through wire or an insulated case. It is understood that the polarity of the anode 322 may be reversed as necessary to remain opposite the electrodes 312. In one embodiment, the electrode 322 on the housing 302, is an anode, and the electrodes 312 in the conduit 304 are cathodes. Preferably, each lead 310 includes a wire which feeds through the housing 302, and is insulated therefrom, and is connected to the circuitry within the housing 302. The case electrode 322 is insulated from the housing and from the electrodes 312.

Referring to FIG. 23, the size of the openings 314 varies. One way to vary the intensity of electrical field at each electrode 312 is to provide a relatively larger or smaller opening 314 at each corresponding electrode 312. For instance, the opening 314' is relatively small while the opening 314"" is relatively large, which will allow a greater intensity of electrical field to be emitted from electrode 312"" as compared to the electrical field emitted from the electrode 312'. The size of any given opening 314 may be chosen to provide a preferred intensity of electrical field at each electrode 312.

Referring to FIG. 23, the size of the openings 314 varies. One way to vary the intensity of electrical field at each electrode 312 is to provide a relatively larger or smaller opening 314 at each corresponding electrode 312. For instance, the opening 314' is relatively small while the opening 314"" is relatively large, which will allow a greater intensity of electrical field to be emitted from electrode 312"" as compared to the electrical field emitted from the electrode 312'. The size of any given opening 314 may be chosen to provide a preferred intensity of electrical field at each electrode 312.

The size of a given opening 314 is 0.5-3 mm, and is chosen such that the total electrode surface area—the surface area defined by the combined surface area of each electrode 312 at each of the several openings 314—is large enough to safely inject the charge needed without electrode or tissue damage. One suitable material from which the electrodes 312 are formed is platinum, and a suitable total surface area of the combined exposed platinum electrodes is 10-14 square millimeters. The spacing between adjacent openings 317, as measured from the center of one opening to the center of the adjacent opening, is proportional to the size of one of the openings 305, as shown in FIGS. 24 and 25. In one instance, the size 315 of a given opening 314 is 20-80% of the spacing 317 to an adjacent opening, as measured from the center of the first opening to the center of the second opening. The spacing 317 between adjacent openings is 1-10 mm, preferably, 2.5 mm and 3.75 mm depending on the size 315 of a given opening. The size 315 of a given opening is preferably between 0.5 mm and 3 mm. In one instance, all openings on the conduit 304 are the same size and the spacing therebetween is the same. In another instance, the size of the openings vary, while the spacing therebetween is the same. In a further instance, the size of each opening is the same, while the spacing therebetween varies. In a still further instance, both the size of the openings and the spacing therebetween varies. These various instances are illustrated in FIGS. 20-23. The configuration which is chosen for a given patient is determined by the particular configuration of acupoints on the patient and the desired stimulation regime at each of the acupoints.

Use and Operation

With the implantable electroacupuncture device (IEAD) 100 in hand, the IDEA 100 may be used most effectively to treat Parkinson's disease and/or Essential Tremor by first pre-setting stimulation parameters that the device will use during a stimulation session. FIG. 15A shows a timing waveform diagram illustrating the EA stimulation parameters used by the IEAD to generate EA stimulation pulses. As seen in FIG. 15A, there are basically four parameters associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01. The duration of a stimulation session is defined by the time period T3. The amplitude of the stimulus pulses is defined by the amplitude A1. This amplitude may be expressed in either voltage or current.

Figure 15B:
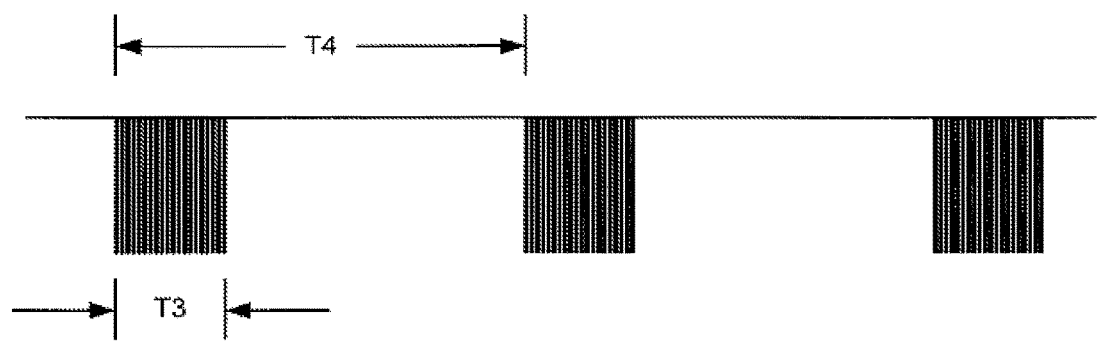
FIG. 15B shows a timing waveform diagram of multiple stimulation sessions, and illustrates the waveforms on a more condensed time scale.

Turning next to FIG. 15B, a timing waveform diagram is shown that illustrates the manner in which the stimulation sessions are administered in accordance with a preferred stimulation regimen. FIG. 15B shows several stimulation sessions of duration T3, and how often the stimulation sessions occur. The stimulation regimen thus includes a time period T4 which sets the time period from the start of one stimulation session to the start of the next stimulation session. T4 thus is the period of the stimulation session frequency, and the stimulation session frequency is equal to 1/T4.

In order to allow the applied stimulation to achieve its desired effect on the body tissue at the selected target stimulation site, the period of the stimulation session T4 may be varied when the stimulation sessions are first applied. This can be achieved by employing a simple algorithm within the circuitry of the EA device that changes the value of T4 in an appropriate manner. For example, at start up, the period T4 may be set to a minimum value, T4(min). Then, as time goes on, the value of T4 is gradually increased until a desired value of T4, T4(final), is reached.

By way of example, if T4(min) is 1 day, and T4(final) is 7 days, the value of T4 may vary as follows once the stimulation sessions begin: T4=1 day for the duration between the first and second stimulation sessions, then 2 days for the duration between the second and third stimulation sessions, then 4 days for the duration between the third and fourth stimulation sessions, and then finally 7 days for the duration between all subsequent stimulation sessions after the fourth stimulation session.

Rather than increasing the value of T4 from a minimum value to a maximum value using a simple doubling algorithm, as described in the previous paragraph, an enhancement is to use a table of session durations and intervals whereby the automatic session interval can be shorter for the first week or so. For example the 1st 30 minute session could be delivered after 1 day. The 2nd 30 minute session could be delivered after 2 days. The 3rd 30 minute session could be delivered after 4 days. Finally, the 4th 30 minute session could be delivered for all subsequent sessions after 7 days.

If a triggered session is delivered completely, it advances the therapy schedule to the next table entry.

Another enhancement is that the initial set amplitude only takes effect if the subsequent triggered session is completely delivered. If the first session is aborted by a magnet application, or by some other control mechanism, the device reverts to a Shelf Mode. In this way, the first session is always a triggered session that occurs in the clinician setting.

Finally, the amplitude and place in the session table are saved in non-volatile memory when they change. This avoids a resetting of the therapy schedule and need to reprogram the amplitude in the event of a device reset.

One preferred set of parameters to use to define a stimulation regimen are

T1=0.5 milliseconds
T2=500 milliseconds
T3=60 minutes
T4=7 days (10,080 minutes)
A1=12 volts (across 1 kOhm), or 12 milliamperes (mA)

It is to be emphasized that the values shown above for the stimulation regimen are representative of only one preferred stimulation regimen that could be used. Other stimulation regimens that could be used, and the ranges of values that could be used for each of these parameters, are as defined in the claims.

It is also emphasized that the ranges of values presented in the claims for the parameters used with the invention have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery itself to be small (coin cell size), which in turn allows the IEAD housing to be very small, which makes the IEAD ideally suited for being used without leads, thereby making it relatively easy to implant the device at the desired acupuncture site, but it also limits the frequency and duration of stimulation sessions.

Limiting the frequency and duration of the stimulation sessions is a key aspect of applicants' invention because it recognizes that some treatments, such as treating Parkinson's disease and/or Essential Tremor, are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). In addition, this slow and methodical conditioning is consistent with the time scale for remodeling of the central nervous system needed to produce the sustained therapeutic effect. Thus, applicants have based their treatment regimens on the slow-and-methodical approach, as opposed to the immediate-and-forced approach adopted by many, if not most, prior art implantable electrical stimulators.

Once the stimulation regimen has been defined and the parameters associated with it have been pre-set into the memory of the micro-controller circuit 220, the IEAD 100 needs to be implanted. Implantation is usually a simple procedure, and is described above in connection with the description of FIGS. 1A. 1B, 1C and 1D, as well as FIGS. 17A and/or 17B.

For treating Parkinson's disease and Essential Tremor, the specified acupoint(s) (or target tissue locations) at which the EA stimulation pulses should be applied in accordance with a selected stimulation regimen are selected from the group of acupoints that comprise GB34, GV20 and the acupoints on the chorea line.

Figure 16:
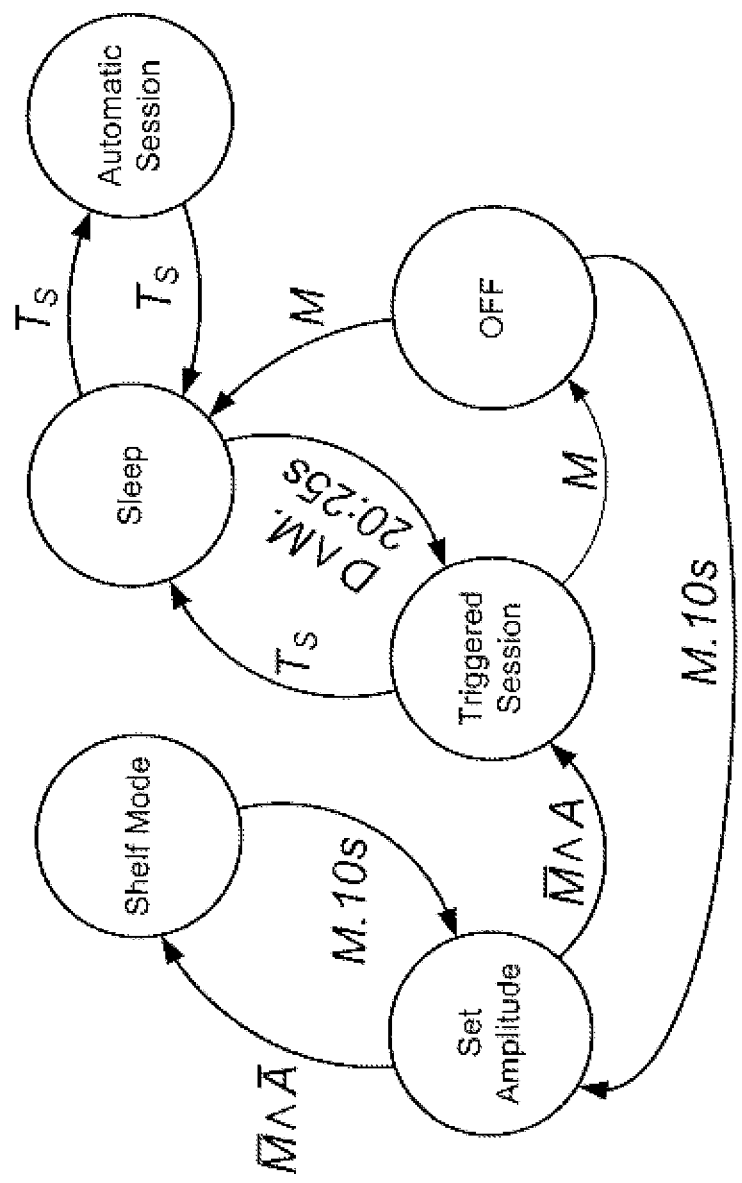
FIG. 16 shows a state diagram that shows the various states in which the IEAD may be placed through the use of an external magnet.

After implantation, the IEAD must be turned ON, and otherwise controlled, so that the desired stimulation regimen may be carried out. In one preferred embodiment, control of the IEAD after implantation, as well as anytime after the housing of the IEAD has been hermetically sealed, is performed as shown in the state diagram of FIG. 16. Each circle shown in FIG. 16 represents a "state" that the micro-controller U2 (in FIG. 13A or 14) may operate in under the conditions specified. As seen in FIG. 16, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M.10 s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero ($\overline{M}AA$), the device continues into the "Triggered Session" so the patient receives the initial therapy. If the magnet is removed during "Set Amplitude" while the amplitude is zero ($\overline{M}A\overline{A}$), the device returns to the Shelf Mode.

The Triggered Session ends and stimulation stops after the session time ($T_S$) has elapsed and the device enters the "Sleep" state. If a magnet is applied during a Triggered Session (M), the session aborts to the "OFF" state. If the magnet remains held on for 10 seconds (M.10 s) while in the "OFF" state, the "Set Amplitude" state is entered with the stimulation level starting from zero amplitude as described.

If the magnet is removed ($\overline{M}$) within 10 seconds while in the OFF state, the device enters the Sleep state. From the Sleep state, the device automatically enters the Automatic Session state when the session interval time has expired ($T_I$). The Automatic Session delivers stimulation for the session time ($T_S$) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M.20:25 s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. This abort of a triggered session by magnet application will not reset the timer, the Triggered Session must be completely delivered.

The circuitry that sets the various states shown in FIG. 16 as a function of externally-generated magnetic control commands, or other externally-generated command signals, is the micro-controller U2 (FIG. 14), the processor U2 (FIG. 13A), or the control circuit 220 (FIGS. 10, 11 and 12). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 14) for controlling the states of the IEAD as shown in FIG. 16 is found in Appendix C.

The use and operation of the IEAD described in this section also applies to the IEAD 300. The IEAD 300 is suitable for operating under the same programming, operation, timing and related parameters described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense and are not intended to be exhaustive or to limit the invention to any precise form disclosed. Many modifications and variations are possible in light of the above teaching. Thus, while the invention(s) herein disclosed has (have) been described by means of specific embodiments and applications thereof, numerous modifications and variations could be made thereto by those skilled in the art without departing from the scope of the invention(s) set forth in the claims.

What is claimed is:

1. An Implantable ElectroAcupuncture System (IEAS) configured to treat Parkinson's disease or Essential Tremor of a patient, comprising:
an implantable electroacupuncture (EA) device comprising a hermetically-sealed housing containing a primary power source and pulse generation circuitry powered by the primary power source, wherein the pulse generation circuitry is configured to generate stimulation pulses in accordance with a specified stimulation regimen;
a plurality of leads in electrical communication with the pulse generation circuitry and defining a plurality of electrodes that are individually controllable by the pulse generation circuitry, wherein each lead included in the plurality of leads defines a particular electrode included in the plurality of electrodes; and
a conduit extending from the housing and carrying the plurality of leads, the conduit comprising a first opening pair that includes a first opening and a second opening formed through the conduit and longitudinally spaced along a length of the conduit, wherein a first electrode included in the plurality of electrodes is located proximate to the first opening and a second electrode included in the plurality of electrodes is located proximate to the second opening;
wherein the pulse generation circuitry is configured to apply the stimulation pulses to one or more acupoints along a chorea line within the patient by way of the first and second electrodes and through the first and second openings.

2. An Implantable ElectroAcupuncture System (IEAS) configured to treat Parkinson's disease or Essential Tremor within a patient, comprising:
an implantable electroacupuncture (EA) device comprising a hermetically-sealed housing containing a primary power source and pulse generation circuitry powered by the primary power source, wherein the pulse generation circuitry is configured to generate stimulation pulses in accordance with a specified stimulation regimen, wherein a portion of an outside of the housing electrically coupled with the pulse generation circuitry and defines a first electrode having a first polarity;
a single lead in electrical communication with the pulse generation circuitry and defining a second electrode having a second polarity; and
a conduit extending from the housing and carrying the single lead, the conduit comprising a first opening pair that includes a first opening and a second opening formed through the conduit and longitudinally spaced along a length of the conduit, the second electrode located proximate to the first and second openings;
wherein the first opening and the second opening each have a longitudinal length as defined by a dimension of the first and second openings measured along a longitudinal length of the conduit, the longitudinal length of the first opening is 20-80% of a longitudinal distance between a center of the first opening and a center of the second opening, and
wherein the pulse generation circuitry is configured to apply the stimulation pulses to one or more acupoints along a chorea line within the patient by way of the first and second electrodes and through the first and second openings.

3. The IEAS of claim 2, wherein the longitudinal length of the second opening is 20-80% of the longitudinal distance between the center of the first opening and a center of the second opening.

4. The IEAS of claim 3, wherein the longitudinal length of the first opening is the same as the longitudinal length of the second opening.

5. The IEAS of claim 4, wherein the conduit further comprises a second opening pair that includes a third opening and a fourth opening formed through the conduit and longitudinally spaced along the length of the conduit, the second electrode also located proximate to the third and fourth openings.

6. The IEAS of claim 5, wherein the longitudinal distance between the first and second openings is the same as a longitudinal distance between the third and fourth openings.

7. The IEAS of claim 5, wherein the longitudinal distance between the first and second openings is different than a longitudinal distance between the third and fourth openings.

8. The IEAS of claim 2, wherein the longitudinal length of the first opening is different than the longitudinal length of the second opening.

9. The IEAS of claim 8, wherein the conduit further comprises a second opening pair that includes a third opening and a fourth opening formed through the conduit and longitudinally spaced along the length of the conduit, the second electrode also located proximate to the third and fourth openings.

10. The IEAS of claim 9, wherein the longitudinal distance between the first and second openings is the same as the longitudinal distance between the third and fourth openings.

11. The IEAS of claim 9, wherein the longitudinal distance between the first and second openings is different than the longitudinal distance between the third and fourth openings.

12. The IEAS of claim 2, wherein the first and second openings each vary in size according to an intensity of the stimulation pulses necessary to treat a given location on the chorea line.

13. An Implantable ElectroAcupuncture System (IEAS) configured to treat Parkinson's disease or Essential Tremor within a patient, comprising:
- an implantable electroacupuncture (EA) device comprising a hermetically-sealed housing containing a primary power source and pulse generation circuitry powered by the primary power source, wherein the pulse generation circuitry is configured to generate stimulation pulses in accordance with a specified stimulation regimen;
- a plurality of leads in electrical communication with the pulse generation circuitry and defining a plurality of electrodes, wherein each lead included in the plurality of leads defines a particular electrode included in the plurality of electrodes; and
- a conduit extending from the housing and carrying the plurality of leads, the conduit comprising a first opening pair that includes a first opening and a second opening formed through the conduit and longitudinally spaced along a length of the conduit, wherein a first electrode included in the plurality of electrodes is located proximate to the first opening and a second electrode included in the plurality of electrodes is located proximate to the second opening;
- wherein the first opening and the second opening each have a longitudinal length as defined by a dimension of the first and second openings as measured along a longitudinal length of the conduit, the longitudinal length of the first opening is 20-80% of a longitudinal distance between a center of the first opening and a center of the second opening, and
- wherein the pulse generation circuitry is configured to apply the stimulation pulses to one or more acupoints along a chorea line within the patient by way of the first and second electrodes and through the first and second openings.

14. The IEAS of claim 13, wherein the longitudinal length of the second opening is 20-80% of the longitudinal distance between the center of the first opening and a center of the second opening.

15. The IEAS of claim 14, wherein:
- the plurality of electrodes further comprises a third electrode and a fourth electrode;
- the conduit further comprises a second opening pair that includes by a third opening and a fourth opening formed through the conduit and longitudinally spaced along the length of the conduit, the third electrode located proximate to the third opening and the fourth electrode located proximate to the fourth opening.

16. The IEAS of claim 15, wherein the longitudinal distance between the first and second openings is the same as a longitudinal distance between the third and fourth openings.

17. The IEAS of claim 15, wherein the longitudinal distance between the first and second openings is different than the longitudinal distance between the third and fourth openings.

* * * * *